(12) United States Patent
Katagiri et al.

(10) Patent No.: US 12,312,323 B2
(45) Date of Patent: May 27, 2025

(54) COMPOUND, METHOD FOR PRODUCING SAME, RESIN COMPOSITION, RESIN SHEET, MULTILAYER PRINTED WIRING BOARD, AND SEMICONDUCTOR DEVICE

(71) Applicant: MITSUBISHI GAS CHEMICAL COMPANY, INC., Tokyo (JP)

(72) Inventors: Shunsuke Katagiri, Tokyo (JP); Takuya Suzuki, Tokyo (JP); Seiji Shika, Tokyo (JP); Yune Kumazawa, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 577 days.

(21) Appl. No.: 17/784,142

(22) PCT Filed: Dec. 9, 2020

(86) PCT No.: PCT/JP2020/045848
§ 371 (c)(1),
(2) Date: Jun. 10, 2022

(87) PCT Pub. No.: WO2021/117764
PCT Pub. Date: Jun. 17, 2021

(65) Prior Publication Data
US 2023/0062796 A1 Mar. 2, 2023

(30) Foreign Application Priority Data

Dec. 11, 2019 (JP) .................. 2019-223952

(51) Int. Cl.
*C07C 69/75* (2006.01)
*C07D 307/83* (2006.01)
(Continued)

(52) U.S. Cl.
CPC ............ *C07D 307/83* (2013.01); *C07C 69/75* (2013.01); *C08F 2/50* (2013.01); *C08F 222/40* (2013.01);
(Continued)

(58) Field of Classification Search
None
See application file for complete search history.

(56) References Cited

U.S. PATENT DOCUMENTS

| 2002/0136987 A1 | 9/2002 | Oshima |
| 2018/0099484 A1 | 4/2018 | Kobayashi et al. |
| 2019/0281697 A1 | 9/2019 | Abe et al. |

FOREIGN PATENT DOCUMENTS

| CN | 1356593 A | 7/2002 |
| CN | 107099026 A | 8/2017 |

(Continued)

OTHER PUBLICATIONS

Polizos, G. et al., "Temperature and pressure effects on molecular mobility and ionic conductivity in telechelics based on poly(ethylene oxide) capped with hydroxyl groups at both ends". Journal of Non-Crystalline Solids 2002, 305(1-3), 212-217. (Year: 2002).*

(Continued)

*Primary Examiner* — Richard A. Huhn
(74) *Attorney, Agent, or Firm* — GREENBLUM & BERNSTEIN, P.L.C.

(57) ABSTRACT

The compound (A) is represented by formula (1).

$$R_1O-R_2-OR_1 \qquad (1)$$

(In formula (1), each $R_1$ independently represents a group represented by formula (2), or a hydrogen atom, and $R_2$ represents a linear or branched alkylene group having 1 to 16 carbon atoms, or a linear or branched alkenylene group (Continued)

having 2 to 16 carbon atoms, provided that at least one $R_1$ is a group represented by formula (2).)

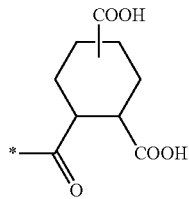

(2)

(In formula (2), -* represents a bonding hand.).

13 Claims, 6 Drawing Sheets

(51) Int. Cl.
| | |
|---|---|
| *C08F 2/50* | (2006.01) |
| *C08F 222/40* | (2006.01) |
| *C08J 5/18* | (2006.01) |
| *C07C 61/08* | (2006.01) |
| *C07C 69/003* | (2006.01) |
| *C07C 69/007* | (2006.01) |

(52) U.S. Cl.
CPC ............... *C08J 5/18* (2013.01); *C07C 61/08* (2013.01); *C07C 69/003* (2013.01); *C07C 69/007* (2013.01); *C08J 2333/24* (2013.01)

(56) References Cited

FOREIGN PATENT DOCUMENTS

| | | |
|---|---|---|
| CN | 107614566 A | 1/2018 |
| CN | 108699216 A | 10/2018 |
| CN | 109415491 A | 3/2019 |
| EP | 1195646 A | 4/2002 |
| EP | 1 195 646 B1 | 2/2005 |
| JP | 2002-107918 A | 4/2002 |
| JP | 2015-229734 A | 12/2015 |
| WO | 2018/056466 A1 | 3/2018 |

OTHER PUBLICATIONS

Noh, Se Hee et al., "Synthesis and Application of Water-Based Urethane Acrylate Crosslinking Agent Containing Unsaturated Group", Journal of Applied Polymer Science, vol. 78, Mar. 9, 2000, pp. 1216-1223.
International Search Report and Written Opinion of the International Searching Authority issued in International Patent Application No. PCT/JP2020/045848, dated Feb. 2, 2020, along with an English translation thereof.
Anonymous: "alkenes" in: "IUPAC Compendium of Chemical Terminology", Feb. 24, 2014, IUPAC, Research, Triangle Park, NC, XP055219897.

* cited by examiner

COMPOUND, METHOD FOR PRODUCING SAME, RESIN COMPOSITION, RESIN SHEET, MULTILAYER PRINTED WIRING BOARD, AND SEMICONDUCTOR DEVICE

TECHNICAL FIELD

The present invention relates to a compound, a method for producing the same, a resin composition, a resin sheet, a multilayer printed wiring board, and a semiconductor device.

BACKGROUND ART

Due to the downsizing and densification of multilayer printed wiring boards, studies have been actively conducted to make the laminate used for multilayer printed wiring boards thinner. Along with the thinning, the insulation layer also needs to be made thinner, and a resin sheet not containing glass cloth has been demanded. The resin composition used as the material of the insulation layer is mainly a thermosetting resin, and drilling of holes between insulation layers to obtain conduction is generally carried out by laser processing.

Meanwhile, the drilling of holes by laser processing has a problem that the processing time becomes longer as the number of holes in a high density substrate becomes larger. In recent years, therefore, there has been a demand for a resin sheet that enables batch drilling in the exposure and development steps by using a resin composition in which an exposed portion is cured by irradiation of rays of light or the like (exposure step) and an unexposed portion can be removed (development step).

As the method of exposure, a method in which a mercury lamp is used as a light source and the exposure is carried out via a photomask is used. A material which can be suitably exposed in the method using a mercury lamp as a light source has been demanded. In the exposure method using a mercury lamp as a light source, a ghi line (a g-line with a wavelength of 436 nm, an h-line with a wavelength of 405 nm and an i-line with a wavelength of 365 nm) or the like is used, and a general-purpose photo initiator can be selected. Also, in recent years, the introduction of a direct imaging method, in which a pattern is directly drawn on the photosensitive resin composition layer without using a photomask, based on digital data of the pattern, has also been progressing as the exposure method. Since this direct imaging method provides better alignment accuracy than the exposure method using a photomask and produces a more detailed pattern, the introduction of this method has been progressing, especially for substrates that require the formation of high density wiring. The light source for this method is a monochromatic light source such as a laser, and in particular, a light source with a wavelength of 405 nm (h-line) is used in devices based on the DMD (Digital Micromirror Device) system, which is capable of forming highly detailed resist patterns.

As a development method, alkaline development is employed because a highly detailed pattern can be obtained.

Patent Document 1 describes a resin composition containing a bismaleimide compound (a curable resin) and a photo radical polymerization initiator (a curing agent) as a photosensitive resin composition used for laminates and resin sheets.

Patent Document 2 describes a resin composition containing a curable resin such as an epoxy resin and a polyvalent carboxy group-containing compound obtained by reacting bismaleimide with a monoamine, and then reacting an acid anhydride. Furthermore, Patent Document 2 describes a polyvalent carboxy group-containing compound which enables production of a cured product having alkaline-developability.

CITATION LIST

Patent Document

Patent Document 1: International Publication No. WO 2018/56466 (A1)
Patent Document 2: Japanese Patent Laid-Open No. 2015-229734

SUMMARY OF INVENTION

Technical Problem

However, in Patent Document 1, a bismaleimide compound is used as a curable resin, but since the maleimide compound normally has poor light transmissivity, when the maleimide compound is contained, light does not reach the photo initiator sufficiently, the photo initiator has difficulty generating radicals, and its reactivity is very low. Therefore, in Patent Document 1, the maleimide compound is cured by additional heating before development, and highly detailed resist patterns cannot be obtained because heating is performed. Since originally, the resin composition described in Patent Document 1 does not have sufficient alkaline-developability, an unexposed resin composition remains even after development. This also suggests that in Patent Document 1, a highly detailed resist pattern cannot be obtained, and the resin composition cannot be used for production of high density printed wiring boards.

For obtaining the polyvalent carboxy group-containing compound described in Patent Document 2, it is necessary to react bismaleimide with a monoamine and then react an acid anhydride, so that the process is complicated. In addition, an aromatic amine compound is used as the monoamine, and therefore the polyvalent carboxy group-containing compound contains an amide group having an aromatic ring in the structure thereof. Thus, the polyvalent carboxy group-containing compound is poor in light transmissivity, hinders photocuring reaction, and is therefore difficult to use for photosensitive resin compositions in reality.

The present invention has been made in view of the problems of such conventional techniques, and an object of the present invention is to provide a compound which does not inhibit a photocuring reaction in an exposure step and is capable of imparting excellent alkaline developability in a development step when used for production of a multilayer printed wiring board; and a resin composition, a resin sheet, a multilayer printed wiring board and a semiconductor device containing the compound.

Solution to Problem

As a result of diligent research, the inventors have found that by using a compound containing a specific carboxyl group in the exposure step and development step of the production of a multilayer printed wiring board, it is possible to obtain a suitably cured product without inhibiting the photocuring reaction and to impart excellent alkaline developability to a resin composition, leading to completion of the present invention.

More specifically, the present invention includes the following contents.

[1] A compound (A) represented by the following formula (1):

wherein each $R_1$ independently represents a group represented by the following formula (2), or a hydrogen atom, and $R_2$ represents a linear or branched alkylene group having 1 to 16 carbon atoms, or a linear or branched alkenylene group having 2 to 16 carbon atoms; provided that at least one $R_1$ is a group represented by the following formula (2):

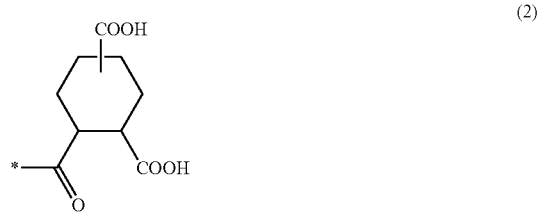

wherein -* represents a bonding hand.

[2] The compound (A) according to [1], wherein at least one $R_1$ is a group represented by the following formula (3):

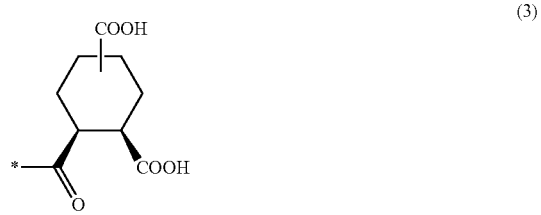

wherein -* represents a bonding hand.

[3] A method for producing the compound (A) according to [1] or [2], containing a step of reacting an alcohol compound represented by the following formula (4) with an acid anhydride represented by the following formula (5):

wherein $R_3$ represents a linear or branched alkylene group having 1 to 16 carbon atoms, or a linear or branched alkenylene group having 2 to 16 carbon atoms.

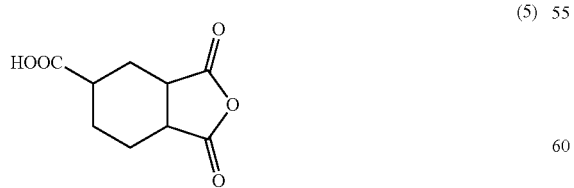

[4] The production method according to [3], wherein the acid anhydride represented by the above formula (5) contains an acid anhydride represented by the following formula (6):

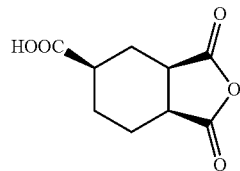

[5] A resin composition containing the compound (A) according to [1] or [2].

[6] The resin composition according to [5], further containing a bismaleimide compound (B) containing a constituent unit represented by the following formula (7), and maleimide groups at both ends of the molecular chain:

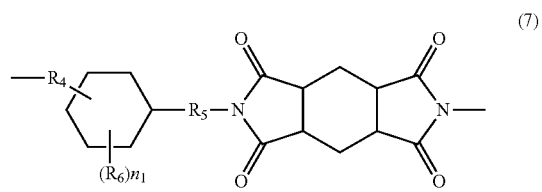

wherein $R_4$ represents a linear or branched alkylene group having 1 to 16 carbon atoms, or a linear or branched alkenylene group having 2 to 16 carbon atoms; $R_5$ represents a linear or branched alkylene group having 1 to 16 carbon atoms, or a linear or branched alkenylene group having 2 to 16 carbon atoms; each $R_6$ independently represents a hydrogen atom, a linear or branched alkyl group having 1 to 16 carbon atoms, or a linear or branched alkenyl group having 2 to 16 carbon atoms; and each $n_1$ independently represents an integer of 1 to 10.

[7] The resin composition according to [5] or [6], further containing at least one maleimide compound (C) selected from the group consisting of a compound represented by the following formula (8), a compound represented by the following formula (9), a compound represented by the following formula (10), a compound represented by the following formula (11), a compound represented by the following formula (12), and a compound represented by the following formula (13):

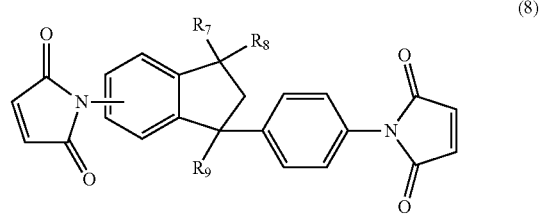

wherein $R_7$, $R_8$ and $R_9$ each independently represent a hydrogen atom, or a linear or branched alkyl group having 1 to 8 carbon atoms and optionally having a substituent;

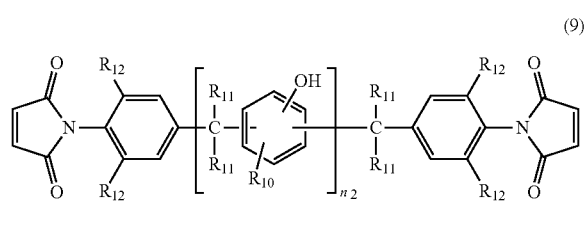
(9)

wherein $R_{10}$, $R_{11}$ and $R_{12}$ each independently represent a hydrogen atom, a hydroxyl group, or a linear or branched alkyl group having 1 to 6 carbon atoms and optionally having a substituent; and $n_2$ represents an integer of 1 to 10;

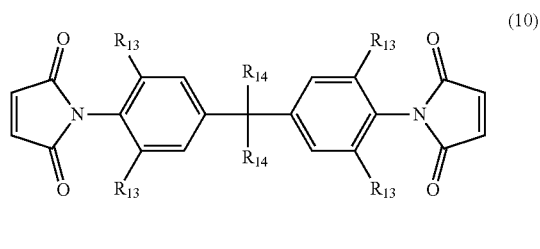
(10)

wherein each $R_{13}$ independently represents a hydrogen atom, a methyl group, or an ethyl group; and each $R_{14}$ independently represents a hydrogen atom or a methyl group;

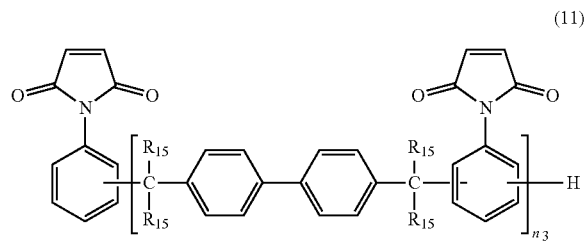
(11)

wherein each $R_{15}$ independently represents a hydrogen atom or a methyl group; and $n_3$ represents an integer of 1 to 10;

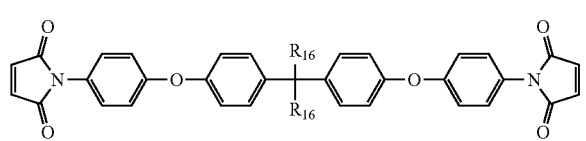
(12)

wherein each $R_{16}$ independently represents a hydrogen atom, a methyl group, or an ethyl group;

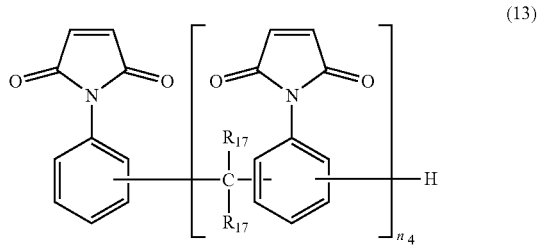
(13)

wherein each $R_{15}$ independently represents a hydrogen atom or a methyl group; and $n_4$ represents an integer of 1 to 10.

[8] The resin composition according to any one of [5] to [7], further containing a photo initiator (D).

[9] The resin composition according to [8], wherein the photo initiator (D) contains a compound represented by the following formula (14):

(14)

wherein each $R_{18}$ independently represents a group represented by the following formula (15) or a phenyl group;

(15)

wherein -* represents a bonding hand, and each $R_{19}$ independently represents a hydrogen atom or a methyl group.

[10] A resin sheet containing a support; and a resin layer disposed on one surface or both surfaces of the support, wherein the resin layer contains the resin composition according to any of [5] to [9].

[11] The resin sheet according to [10], wherein the resin layer has a thickness of 1 to 50 μm.

[12] A multilayer printed wiring board containing an insulation layer; and a conductor layer formed on one surface or both surfaces of the insulation layer, wherein the conductor layer contains the resin composition according to any of [5] to [9].

[13] A semiconductor device containing the resin composition according to any of [5] to [9].

Advantageous Effects of Invention

According to the present invention, by using a compound containing a specific carboxyl group in the exposure step and development step of the production of a multilayer printed wiring board, it is possible to provide a compound which allows to obtain a suitably cured product without inhibiting the photocuring reaction and to impart excellent alkaline developability to a resin composition; and a resin composition, a resin sheet, a multilayer printed wiring board and a semiconductor device containing the compound.

DESCRIPTION OF EMBODIMENT

Figure 1:
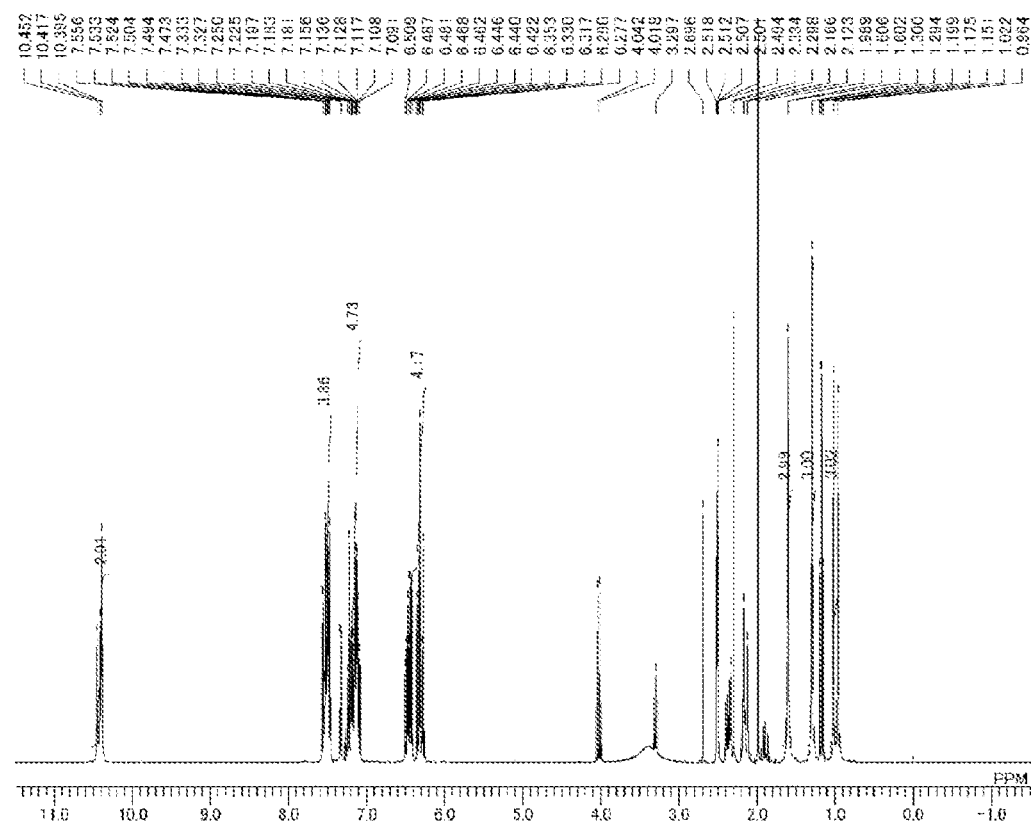
FIG. 1 shows the $^1$H-NMR chart of an amide acid compound (MA-TMDA).

Hereinafter, an embodiment for carrying out the present invention (hereinafter, referred to as the "present embodiment") will be described in detail. The present embodiment described below is only illustrative of the present invention and is not intended to limit the present invention to the contents of the following description. The present invention can be carried out with appropriate modifications falling within the gist of the invention.

Note that, in the present specification, the term "(meth)acryloxy" refers to both "acryloxy" and "methacryloxy" corresponding thereto, and the term "(meth)acryl" refers to both "acryl" and "methacryl" corresponding thereto. Also, in the present embodiment, "resin solid content" or "resin solid content in a resin composition" refers to components in a resin composition excluding a compound (A), a photo initiator (D), an additive agent, a solvent, and a filler unless otherwise noted, and "100 parts by mass of resin solid content" refers to the total of components in a resin composition excluding a compound (A), a photo initiator (D), an additive agent, a solvent, and a filler being 100 parts by mass.

The compound (A) of the present embodiment will be described.

[Compound (A)]

The compound (A) (also referred to as component (A)) of the present embodiment is represented by formula (1):

$$R_1O-R_2-OR_1 \quad (1)$$

In the formula (1), each $R_1$ independently represents a group represented by formula (2), or a hydrogen atom, and $R_2$ represents a linear or branched alkylene group having 1 to 16 carbon atoms, or a linear or branched alkenylene group having 2 to 16 carbon atoms. provided that at least one $R_1$ is a group represented by formula (2):

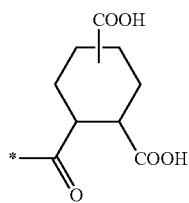

(2)

In the formula (2), -* indicates a bonding hand to an oxygen atom (O) directly bonded to $R_1$ in the formula (1).

In the present embodiment, by using a compound (A) in the exposure step and development step of the production of a multilayer printed wiring board, it is possible to obtain a suitably cured product without inhibiting the photocuring reaction and after exposure, to impart excellent alkaline developability to the resin composition in the unexposed portion. The reason for this is not certain, but the present inventors estimate it as follows. That is, in the exposure step of the production of a multilayer printed wiring board, the compound (A) does not have any functional group involved in the photocuring reaction of the exposure step and does not inhibit the photocuring reaction. The compound (A) also has superior light transmissivity, as it does not have a backbone inhibiting light transmissivity. Therefore, even if the compound (A) is included, photopolymerization proceeds and a cured product can be suitably obtained. Since the compound (A) is not involved in the photocuring reaction, it can be present in the resin composition of the unexposed portion. Therefore, when in the development step, the alkaline developing solution flows into the unexposed portion, the alkaline component in the alkaline developing solution and a carboxy group in the compound (A) can suitably form a salt, which improves water-solubility, thus providing excellent alkaline developability. It is also presumed that the compound (A) can impart excellent alkaline developability by having a plurality of carboxy groups.

The compound (A) has a transmittance of 5% or more when a N-methylpyrrolidone solution containing the compound (A) at 1% by mass is prepared and the transmittance of the N-methylpyrrolidone solution containing the compound (A) at 1% by mass is measured using an active energy ray including a wavelength of 365 nm (i-line). The compound (A) thus exhibits superior light transmissivity. In addition, the compound (A) has a transmittance of 5% or more when the transmittance of a N-methylpyrrolidone solution containing the compound (A) at 1% by mass is measured using an active energy ray including a wavelength of 405 nm (h-line). Even in this case, superior light transmissivity is exhibited. When the compound (A) is used in such a way, for example, upon producing a printed wiring board having a highly dense and highly detailed wiring formation (pattern) using the direct imaging method, for example, the photo radical reaction of the maleimide occurs efficiently even when an active energy ray including a wavelength of 405 nm (h-line) is used. The transmittance at a wavelength of 365 nm (i-line) is preferably 8% or more, more preferably 10% or more, still more preferably 20% or more, even more preferably 30% or more, and furthermore preferably 40% or more because a resin composition that is superior in photocurability can be obtained. The transmittance at a wavelength of 405 nm (h-line) is preferably 8% or more, more preferably 10% or more, still more preferably 20% or more, even more preferably 30% or more, and furthermore preferably 40% or more because a resin composition that is superior in photocurability can be obtained. The upper limit of each of the transmittance at a wavelength of 365 nm (i-line) and the transmittance at a wavelength of 405 nm (h-line) is, for example, 99.9% or less.

In the compound (A), in formula (1), each $R_1$ independently represents a group represented by formula (2) or a hydrogen atom. Since $R_1$ can impart better alkaline developability, it is preferable that the two $R_1$s be groups represented by formula (2). For the groups represented by formula (2), if the position of the carbonyl group is defined as position 1 with respect to the cyclohexane ring, as long as a carboxyl group is bonded at the position 2 with respect to the carbonyl group, another carboxyl group may be bonded to any of the positions 3 to 6 of the cyclohexane ring. In addition, the compound (A) exists in the cis-form, the trans-form, and as a mixture of the cis-form and the trans-form since the structure of the carbonyl group with the two carboxyl groups bonded to the cyclohexane ring in the group represented by formula (2) is a steric structure. That is, the compound (A) may be one isomer alone or a mixture containing two or more isomers.

In formula (1), since $R_1$ can impart better alkaline developability, it is preferable that at least one $R_1$ be a group represented by formula (3). That is, in the group represented by formula (3), the steric structure of the carbonyl group bonded to the position 1 of the cyclohexane ring with the carboxyl group at the position 2 is preferably cis. For the other carboxyl group, its steric structure may be either cis or trans. Since $R_1$ can impart even better alkaline developability, it is preferable that the two R's be groups represented by formula (3). Although it is unclear why better alkaline developability can be imparted when at least one $R_1$ is a group represented by formula (3), the present inventors presume the reason to be as follows. That is, they presume that it is because when the carbonyl group bonded at the position 1 and the carboxyl group bonded at the position 2 are cis, the carboxyl group at the position 2 and the alkali component in the alkaline developing solution can form a steric structure that facilitates the formation of a salt in the resin composition, which further improves water-solubility and further promotes the inflow of the alkaline developing solution into the resin composition.

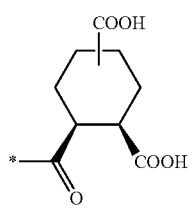

(3)

In the formula (3), -* indicates a bonding hand to an oxygen atom (O) directly bonded to $R_1$ in the formula (1).

In the formula (1), $R_2$ represents a linear or branched alkylene group having 1 to 16 carbon atoms, or a linear or branched alkenylene group having 2 to 16 carbon atoms. $R_2$ is preferably a linear or branched alkylene group from the viewpoint of exhibiting good solubility in a solvent, and is more preferably a linear alkylene group from the viewpoint of exhibiting good solubility in a solvent, imparting better alkaline developability, and exhibiting good compatibility with another resin when made into a resin composition.

The number of carbon atoms in the alkylene group is preferably 2 to 14, and more preferably 4 to 12 from the viewpoint of exhibiting better solubility in a solvent.

Examples of the linear or branched alkylene group include a methylene group, an ethylene group, a propylene group, a 2,2-dimethylpropylene group, a butylene group, a pentylene group, a hexylene group, a heptylene group, an octylene group, a nonylene group, a decylene group, a dodecylene group, an undecylene group, a tridecylene group, a tetradecylene group, a pentadecylene group, a hexadecylene group, a neopentylene group, a dimethylbutylene group, a methylhexylene group, an ethylhexylene group, a dimethylhexylene group, a trimethylhexylene group, a methylheptylene group, a dimethylheptylene group, a trimethylheptylene group, a tetramethylheptylene group, an ethylheptylene group, a methyloctylene group, a methylnonylene group, a methyldecylene group, a methyldodecylene group, a methylundecylene group, a methyltridecylene group, a methyltetradecylene group and a methylpentadecylene group. Among these, a pentylene group, a hexylene group, a heptylene group, an octylene group, a nonylene group, a decylene group, a dodecylene group, and an undecylene group are more preferable from the viewpoint of exhibiting good solubility in a solvent, imparting better alkaline developability, and exhibiting good compatibility with another resin when made into a resin composition.

The number of carbon atoms in the alkenylene group is preferably 2 to 14, and more preferably 4 to 12 from the viewpoint of exhibiting better solubility in a solvent.

Examples of the linear or branched alkenylene group include a vinylene group, a 1-methylvinylene group, an arylene group, a propenylene group, an isopropenylene group, a 1-butenylene group, a 2-butenylene group, a 1-pentenylene group, a 2-pentenylene group, an isopentylene group, a cyclopentenylene group, a 1-hexenylene group, a 2-hexenylene group, a 3-hexenylene group, a cyclohexenylene group and a dicyclopentadienylene group. Among these, a 1-hexenylene group, a 2-hexenylene group, a 3-hexenylene group, a cyclohexenylene group and a dicyclopentadienylene group are more preferable from the viewpoint of exhibiting good solubility in a solvent, imparting better alkaline developability, and exhibiting good compatibility with another resin when made into a resin composition.

The compound (A) is preferably a compound represented by formula (16), a compound represented by formula (17), and a compound represented by formula (18), and more preferably a compound represented by formula (17), and a compound represented by formula (18), from the viewpoint of exhibiting good solubility in a solvent, imparting even better alkaline developability, and further exhibiting good compatibility with another resin when made into a resin composition.

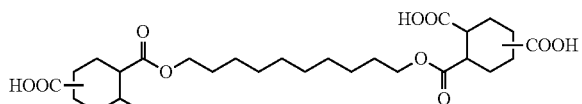

(16)

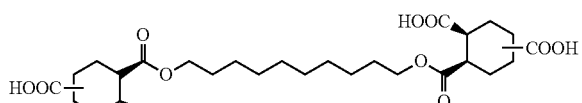

(17)

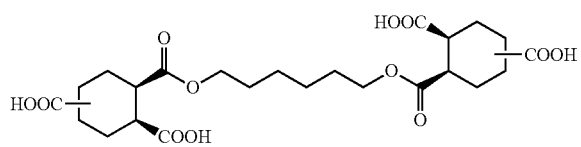

(18)

[Method for Producing Compound (A)]

The compound (A) can be produced by a publicly known method, and for example, can be obtained by including a step of esterification reaction between an alcohol compound represented by formula (4) and an acid anhydride represented by formula (5) (cyclohexane-1,2,4-tricarboxylic acid-1,2-anhydride). Note that the acid anhydride represented by formula (5) exists in the cis-form, the trans-form, and as a mixture of the cis-form and the trans-form since the structure of the two carbonyl groups with the carboxyl group bonded to the cyclohexane ring is a steric structure. That is, the acid anhydride represented by formula (5) may be one isomer alone or a mixture containing two or more isomers.

In the formula (4), $R_3$ represents a linear or branched alkylene group having 1 to 16 carbon atoms, or a linear or branched alkenylene group having 2 to 16 carbon atoms.

For the linear or branched alkylene group having 1 to 16 carbon atoms, or the linear or branched alkenylene group having 2 to 16 carbon atoms, $R_2$ in the above formula (1) can be referred to, including the preferable aspects.

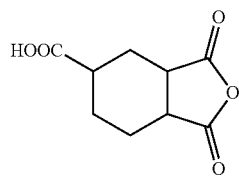

Examples of the alcohol compound represented by formula (4) include methylene glycol, ethylene glycol, 1,3-propanediol, propylene glycol, 1,2-butanediol, 1,3-butanediol, 1,4-butanediol, 1,5-pentanediol, 2,4-pentanediol, 1,6-hexanediol, 2,5-hexanediol, 1,2-hexanediol, 1,8-octanediol, 1,2-octanediol, 1,9-nonanediol, 1,10-decanediol, 1,16-hexadecanediol, 2,2,4-trimethyl-1,3-pentanediol, 2,2-isoamyl-1,3-propanediol, 2,2-diisobutyl-1,3-propanediol, 2,4-diethyl-1,5-pentanediol, 2-butyl-2-ethyl-1,3-propanediol, trans-2-butene-1,4-diol, and cis-2-butene-1,4-diol.

As the acid anhydride represented by formula (5), the acid anhydride represented by formula (6) (cis,cis-cyclohexane-1,2,4-tricarboxylic acid-1,2-anhydride) is preferably included, as it can impart excellent alkaline developability when the cured product is produced using the compound (A). That is, in the acid anhydride represented by formula (6), if the positions of the carbonyl groups are 1 and 2 with respect to the cyclohexane ring, the steric structure of the carbonyl group bonded at position 4 with respect to that carbonyl group, with the two carbonyl groups is preferably cis.

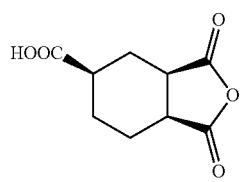

The esterification reaction can be carried out in a solvent or without solvent. The solvent is not particularly limited as long as it is a solvent which does not react with the alcohol compound and acid anhydride.

Examples of such a solvent include halogenated solvents such as dichloromethane, chloroform, dichloroethane, and chlorobenzene; aprotic polar solvents such as dimethylformamide, dimethylacetamide, dimethyl sulfoxide, tetrahydrofuran, dioxane, and acetonitrile; ketone solvents such as acetone, methyl ethyl ketone, methyl isobutyl ketone, cyclopentanone, and cyclohexanone; cellosolve solvents such as 2-ethoxyethanol and propylene glycol monomethyl ether; aliphatic alcohol solvents such as methanol, ethanol, propanol, isopropanol, and butanol; aromatic group-containing phenol solvents such as phenol and cresol; ester solvents such as ethyl lactate, methyl acetate, ethyl acetate, butyl acetate, isoamyl acetate, methyl methoxypropionate, methyl hydroxyisobutyrate, γ-butyrolactone, and propylene glycol monomethyl ether acetate; and aromatic hydrocarbon solvents such as toluene and xylene. These solvents may be used singly, or two or more thereof may be appropriately mixed and used. Among these, halogenated solvents, aprotic polar solvents, ketone solvents, and ester solvents are preferable as they can sufficiently dissolve an alcohol compound and acid anhydride. Moreover, the amount used when using a solvent is normally 20 to 2000 parts by mass based on 100 parts by mass of the total of the alcohol compound and acid anhydride.

The esterification reaction may be performed with or without a catalyst.

If a catalyst is used, examples of the catalyst include acidic compounds such as hydrochloric acid, sulfuric acid, methanesulfonic acid, tri fluoromethanesulfonic acid, para-toluenesulfonic acid, nitric acid, trifluoroacetic acid, and trichloroacetic acid; metal hydroxides such as sodium hydroxide, potassium hydroxide, calcium hydroxide, and magnesium hydroxide; amine compounds such as triethylamine, tripropylamine, diisopropylethylamine, and tributylamine; aliphatic amines having an aromatic ring such as aniline, N-methylaniline, N,N-dimethylaniline, and benzylamine; heterocyclic compounds such as pyridine, 4-dimethylaminopyridine, 1,8-diazabicyclo[5.4.0]undeca-7-ene, imidazole, triazole, and tetrazole; quaternary ammonium salts such as tetramethylammonium hydroxide, tetraethylammonium hydroxide, tetrapropylammonium hydroxide, tetrabutylammonium hydroxide, trimethylethylammonium hydroxide, trimethylpropylammonium hydroxide, trimethylbutylammonium hydroxide, trimethylcetylammonium hydroxide, trioctylmethylammonium hydroxide, tetramethylammonium chloride, tetramethylammonium bromide, tetramethylammonium iodide, tetramethylammonium acetate, and trioctylmethylammonium acetate; orthotitanates such as tetraethyl orthotitanate and tetramethyl orthotitanate; and metal soaps such as tin octylate, cobalt octylate, zinc octylate, manganese octylate, calcium octylate, sodium octylate, and potassium octylate. These catalysts may be used singly, or two or more thereof may be appropriately mixed and used. Among these, amine compounds, aliphatic amines having an aromatic ring, and heterocyclic compounds are preferable, and triethylamine and 4-dimethylaminopyridine are more preferable, from the viewpoint of having good reactivity. Moreover, the amount used when using a catalyst is normally 0.001 to 1000 parts by mass based on 100 parts by mass of the total of the alcohol compound and acid anhydride.

Examples of the method for adding the catalyst include a method of adding it directly to the alcohol compound and/or acid anhydride, and a method of adding a solution in which it is dissolved in a soluble solvent or the like, to the alcohol compound, acid anhydride, and/or a solvent containing them.

The reaction temperature in the esterification reaction is not particularly limited and depends on the amount of catalyst and the solvent used, but is normally −20 to 150° C. The reaction time is also not particularly limited, but is normally 0.5 to 100 hours. The reaction may be completed in one step or in two or more steps.

For the method of isolating the target compound (A) from the reaction mixture containing the compound (A), filtration or centrifugation may be performed for isolation if the target compound precipitates from the reaction solvent. If the target product is dissolved in the reaction solvent, it can be isolated by distilling off the solvent under reduced pressure, adding an appropriate poor solvent to the reaction mixture, or discharging the reaction mixture into the poor solvent to precipitate it, and then filtering or centrifuging it. Note that examples of the poor solvent include hydrocarbons such as hexane, heptane, cyclohexane, toluene, and xylene. These solvents may be used singly, or two or more thereof may be appropriately mixed and used.

If the isolated compound (A) needs to be further purified, it can be purified by employing a publicly known method. Examples of such a method include purification by distillation, recrystallization, column chromatography, sludge treatment, and activated carbon treatment.

The obtained compound (A) can be identified by a publicly known method such as NMR (nuclear magnetic resonance analysis). The purity of the compound (A) can be analyzed by, for example, GPC, liquid chromatography, and IR spectroscopy. The volatile components such as the by-products and residual solvents in the compound (A) can be quantitatively analyzed by, for example, GPC and gas chromatography. The remaining halogen compounds in the compound (A) can be identified by, for example, liquid chromatography-mass spectrometry. The halogen compounds remaining in the compound (A) can also be quantified by ion chromatography after potentiometric titration using a silver nitrate solution or decomposition by a combustion method.

[Resin Composition]

The resin composition of the present embodiment contains the compound (A) and is suitably used in the production of a multilayer printed wiring board. By using a resin composition, it is possible to obtain a suitably cured product without inhibiting the photocuring reaction in the exposure step and development step of the production of a multilayer printed wiring board, and after exposure, to impart excellent alkaline developability.

In the resin composition, the content of the compound (A) is preferably 0.1 to 30 parts by mass, more preferably 0.5 to 15 parts by mass, and still more preferably 1 to 15 parts by mass based on 100 parts by mass of the resin solid content in the resin composition because better alkaline developability can be imparted and good curability can be exhibited without inhibiting the photocuring reaction in the resin composition.

In addition, if the later-described bismaleimide compound (B) and the later-described maleimide compound (C) are contained in the resin composition, the content of the compound (A) is preferably 0.1 to 30 parts by mass, more preferably 0.5 to 15 parts by mass, and still more preferably 1 to 15 parts by mass based on 100 parts by mass of the total of the later-described bismaleimide compound (B) and the later-described maleimide compound (C) because better alkaline developability can be imparted and good curability can be exhibited without inhibiting the photocuring reaction in the resin composition.

[Bismaleimide Compound (B)]

The resin composition of the present embodiment preferably further contains a bismaleimide compound (B) (also referred to as component (B)). The bismaleimide compound (B) contains a constituent unit represented by the formula (7), and maleimide groups at both ends of the molecular chain:

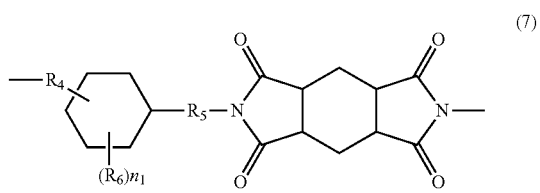

In the formula (7), $R_4$ represents a linear or branched alkylene group having 1 to 16 carbon atoms, or a linear or branched alkenylene group having 2 to 16 carbon atoms. $R_5$ represents a linear or branched alkylene group having 1 to 16 carbon atoms, or a linear or branched alkenylene group having 2 to 16 carbon atoms. Each $R_6$ independently represents a hydrogen atom, a linear or branched alkyl group having 1 to 16 carbon atoms, or a linear or branched alkenyl group having 2 to 16 carbon atoms. Each $n_1$ independently represents an integer of 1 to 10.

Normally, maleimide compounds have extremely low water solubility, do not have reactivity with an alkaline component in an alkaline developing solution, and therefore hardly exhibit alkaline developability. However, by containing the bismaleimide compound (B) along with the compound (A), the resin composition has very good alkaline developability, while having excellent photocurability. The reason for this is not certain, but the present inventors estimate it as follows.

That is, the resin composition contains a compound (A) which does not inhibit the photocuring reaction and can impart excellent alkaline developability to the resin composition. Furthermore, the bismaleimide compound (B) has a relatively long chain and a flexible structure, and does not have a structure which causes interaction with an alkaline component in the alkaline developing solution. Therefore, the bismaleimide compound (B) can be dissolved in the alkaline developing solution as the compound (A) is dissolved in the alkaline developing solution while the structure of the compound (A) is maintained in the alkaline developing solution. Therefore, in the development step, the alkaline developing solution flows into an unexposed portion (resin composition), the alkaline component in the alkaline developing solution and a carboxy group in the compound (A) can quickly and suitably form a salt without being hindered by the bismaleimide compound (B). Thus, water-solubility is improved. This may be the reason why the resin composition has excellent alkaline developability.

Furthermore, the present inventors presume that the reason why the inclusion of the bismaleimide compound (B) with the compound (A) allows the resin composition to have excellent photocuring reactivity is as follows.

Normally, since maleimide compounds have poor light transmissivity, when the resin composition contains a maleimide compound, light does not sufficiently reach the photo initiator dispersed in the resin composition, and the photo initiator has difficulty generating radicals. Therefore, in general, the photo radical reaction of maleimide compounds is difficult to proceed, and even if radical polymerization or dimerization reaction of single maleimide proceeds, its reactivity is very low. The bismaleimide compound (B) contains a constituent unit represented by the formula (7), i.e. an alicyclic backbone, and therefore has superior light transmissivity. The compound (A) also has superior light transmissivity. Therefore, light reaches the photo initiator sufficiently, so that the photo radical reaction of the maleimide efficiently takes place. Using various active energy rays, the compound (A) and the bismaleimide compound (B) can be photocured together with the later-described maleimide compound (C) and the later-described photo initiator (D), which are blended as necessary.

The bismaleimide compound (B) exhibits superior light transmissivity, with a transmittance of 5% or more, when a chloroform solution containing the bismaleimide compound (B) at 1% by mass is prepared and the transmittance of the chloroform solution containing the bismaleimide compound (B) at 1% by mass is measured using an active energy ray including a wavelength of 365 nm (i-line). In addition, the bismaleimide compound (B) exhibits superior light transmissivity, with a transmittance of 5% or more, when the transmittance of the chloroform solution containing the bismaleimide compound (B) at 1% by mass is measured using an active energy ray including a wavelength of 405 nm (h-line). Therefore, for example, upon producing a printed wiring board having a highly dense and highly detailed wiring formation (pattern) using the direct imaging method, the photo radical reaction of the maleimide occurs efficiently even when an active energy ray including a wavelength of 405 nm (h-line) is used. The transmittance at a wavelength of 365 nm (i-line) is preferably 8% or more, more preferably 10% or more, from the viewpoint of exhibiting superior light transmissivity. The transmittance at a wavelength of 405 nm (h-line) is preferably 8% or more, more preferably 10% or more, from the viewpoint of producing a printed wiring board having a more highly dense and highly detailed wiring formation (pattern). The upper limit of each of the transmittance at a wavelength of 365 nm (i-line) and the transmittance at a wavelength of 405 nm (h-line) is, for example, 99.9% or less.

Normally, the absorbance of the photo initiator tends to decrease for light in the long-wavelength region. For example, when an active energy ray (ray of light) including a wavelength of 405 nm (h-line) is used, a usual photo initiator does not absorb the ray because light having such a wavelength has a relatively long wavelength, and polymerization proceeds only when a photo initiator capable of suitably absorbing the light to generate radicals is used. Therefore, as the later-described photo initiator (D), a photo initiator is preferably used which exhibits very excellent absorption of light with a wavelength of 405 nm (h-line), with an absorbance of 0.1 or more, when the absorbance of a chloroform solution containing the photo initiator (D) at 0.01% by mass is measured.

Since the bismaleimide compound (B) has excellent light transmissivity as mentioned above, light reaches the photo initiator sufficiently, for example, even when an active energy ray including a wavelength of 365 nm or an active energy ray including a wavelength of 405 nm is used, radical reaction using radicals generated from the photo initiator proceeds, and even a composition containing a large amount of the bismaleimide compound (B) can be photocured.

Furthermore, the resin composition has excellent alkaline developability and photocurability. The obtained cured product also has excellent heat resistance, insulation reliability, and thermal stability. Therefore, according to the present embodiment, protective films and insulation layers in multilayer printed wiring boards and semiconductor devices can be suitably formed.

The mass average molecular weight of the bismaleimide compound (B) is not particularly limited as long as the effect of the present invention is achieved, but is preferably 100 to 5000, and more preferably 300 to 4500 from the viewpoint that a suitable viscosity can be obtained and an increase in viscosity of varnish can be suppressed. In the present embodiment, the term "mass average molecular weight" means a mass average molecular weight in terms of polystyrene standard by a gel permeation chromatography (GPC) method.

The structure of the bismaleimide compound (B) will now be described.

In the formula (7) of the bismaleimide compound (B), $R_4$ represents a linear or branched alkylene group having 1 to 16 carbon atoms, or a linear or branched alkenylene group having 2 to 16 carbon atoms. $R_4$ is preferably a linear or branched alkylene group, and more preferably a linear alkylene group because a suitable viscosity can be obtained and an increase in viscosity of varnish can be controlled.

The number of carbon atoms in the alkylene group is preferably 2 to 14, and more preferably 4 to 12 because a more suitable viscosity can be obtained and an increase in viscosity of varnish can be more reliably controlled.

For the linear or branched alkylene group, $R_2$ in the above formula (1) can be referred to.

The number of carbon atoms in the alkenylene group is preferably 2 to 14, and more preferably 4 to 12 because a more suitable viscosity can be obtained and an increase in viscosity of varnish can be more reliably controlled.

For the linear or branched alkenylene group, $R_2$ in the above formula (1) can be referred to.

In the formula (7), $R_5$ represents a linear or branched alkylene group having 1 to 16 carbon atoms, or a linear or branched alkenylene group having 2 to 16 carbon atoms. $R_5$ is preferably a linear or branched alkylene group, and more preferably a linear alkylene group because a suitable viscosity can be obtained and an increase in viscosity of varnish can be controlled.

The number of carbon atoms in the alkylene group is preferably 2 to 14, and more preferably 4 to 12 because a more suitable viscosity can be obtained and an increase in viscosity of varnish can be more reliably controlled.

For the linear or branched alkylene group, $R_2$ in the above formula (1) can be referred to.

The number of carbon atoms in the alkenylene group is preferably 2 to 14, and more preferably 4 to 12 because a more suitable viscosity can be obtained and an increase in viscosity of varnish can be more reliably controlled.

For the linear or branched alkenylene group, $R_2$ in the above formula (1) can be referred to.

In the formula (7), $R_4$ and $R_5$ may be the same or different, and are preferably the same because the bismaleimide compound (B) can be more easily synthesized.

In the formula (7), each $R_6$ independently represents a hydrogen atom, a linear or branched alkyl group having 1 to 16 carbon atoms, or a linear or branched alkenyl group having 2 to 16 carbon atoms. It is preferable that each $R_6$ be independently a hydrogen atom or a linear or branched alkyl group having 1 to 16 carbon atoms because a suitable viscosity can be obtained and an increase in viscosity of varnish can be controlled, it is more preferable that one to five groups ($R_6$s) among $R_6$s be linear or branched alkyl groups each having 1 to 16 carbon atoms, and other groups ($R_6$) be hydrogen atoms, and it is still more preferable that one to three groups ($R_6$s) among $R_6$s be linear or branched alkyl groups each having 1 to 16 carbon atoms, and other groups ($R_6$) be hydrogen atoms.

The number of carbon atoms in the alkyl group is preferably 2 to 14, and more preferably 4 to 12 because a more suitable viscosity can be obtained and an increase in viscosity of varnish can be more reliably controlled.

Examples of the linear or branched alkyl group include a methyl group, an ethyl group, a n-propyl group, an isopropyl group, a 1-ethylpropyl group, a n-butyl group, a 2-butyl group, an isobutyl group, a tert-butyl group, a n-pentyl group, a 2-pentyl group, a tert-pentyl group, a 2-methylbutyl group, a 3-methylbutyl group, a 2,2-dimethylpropyl group, a n-hexyl group, a 2-hexyl group, a 3-hexyl group, a n-heptyl group, a n-octyl group, a 2-methylpentyl group, a 3-methylpentyl group, a 4-methylpentyl group, a 2-methylpentan-3-yl group and a n-nonyl group.

The number of carbon atoms in the alkenyl group is preferably 2 to 14, and more preferably 4 to 12 because a more suitable viscosity can be obtained and an increase in viscosity of varnish can be more reliably controlled.

Examples of the linear or branched alkenyl group include a vinyl group, an allyl group, a 4-pentenyl group, an isopropenyl group, an isopentenyl group, a 2-heptenyl group, a 2-octenyl group and a 2-nonenyl group.

In the formula (7), each $n_1$ independently represents an integer of 1 to 10.

The bismaleimide compound (B) has maleimide groups at both ends of the molecular chain. The term "both ends" means both ends of the molecular chain of the bismaleimide compound (B), and for example, when the structural unit represented by the formula (7) is present at an end of the molecular chain of the bismaleimide compound (B), the maleimide group is present at an end of the molecular chain of $R_4$, at an end of the molecular chain on the N atom of the maleimide ring, or at each of both the ends. The bismaleimide compound (B) may have maleimide groups at positions other than both ends of the molecular chain.

The maleimide group is represented by the formula (19), and the N atom is bonded to the molecular chain of the bismaleimide compound (B). In addition, the maleimide groups bonded to the bismaleimide compound (B) may be all the same or different, and the maleimide groups at both ends of the molecular chain are preferably the same.

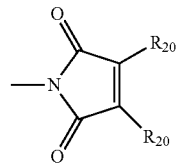

(19)

In the formula (19), each $R_{20}$ independently represents a hydrogen atom, or a linear or branched alkyl group having 1 to 4 carbon atoms. Each $R_{20}$ is preferably a hydrogen atom because photocuring is suitably performed.

The number of carbon atoms in the alkyl group is preferably 1 to 3, and more preferably 1 or 2 because photocuring is suitably performed.

For the linear or branched alkyl group, the above $R_6$ can be referred to.

Examples of such a bismaleimide compound (B) include a maleimide compound represented by the formula (20). These bismaleimide compounds may be used singly, or two or more thereof may be appropriately mixed and used.

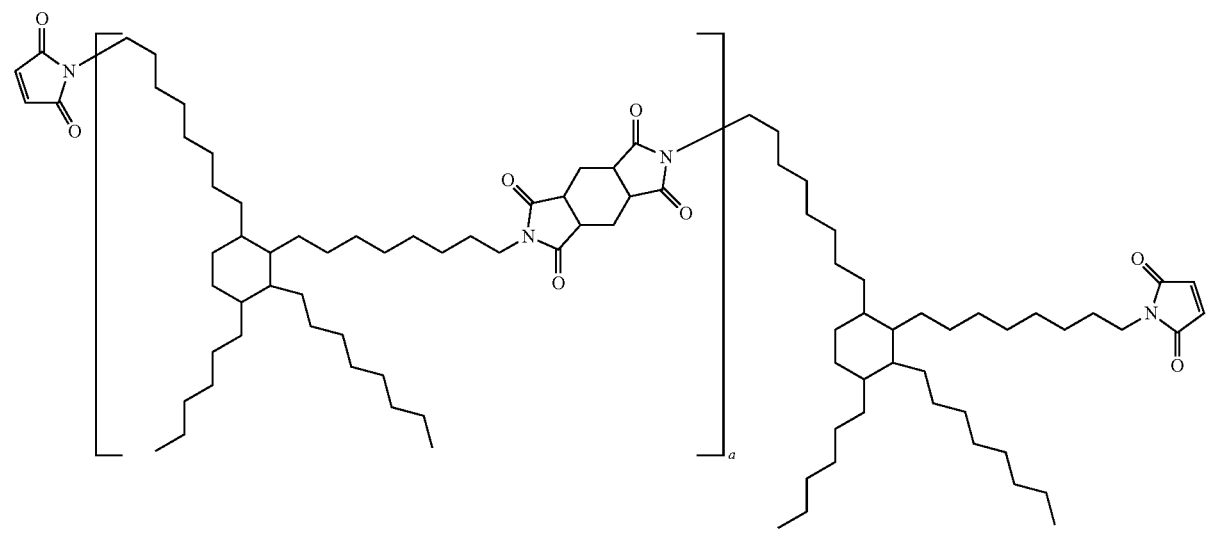

(20)

In the formula (20), a represents an integer of 1 to 10. a is preferably an integer of 1 to 6 because a more suitable viscosity can be obtained and an increase in viscosity of varnish can be more reliably controlled.

As the bismaleimide compound (B), commercial products can also be used. Examples of the commercial products include MIZ-001 manufactured by Nippon Kayaku Co., Ltd. (product name, containing the maleimide compound of the formula (20)).

In the resin composition, the content of the bismaleimide compound (B) is preferably 10 to 90 parts by mass, more preferably 30 to 80 parts by mass, and still more preferably 40 to 70 parts by mass in 100 parts by mass of the resin solid content, from the viewpoint that it becomes possible to obtain a cured product mainly composed of the bismaleimide compounds, that photocurability can be improved, and that better heat resistance and thermal stability are obtained.

In addition, if the bismaleimide compound B and the later-described maleimide compound (C) are contained in the resin composition, the content of the bismaleimide compound (B) is preferably 10 to 90 parts by mass, more preferably 30 to 80 parts by mass, and still more preferably 40 to 70 parts by mass based on 100 parts by mass of the total of the bismaleimide compound (B) and the later-described maleimide compound (C), from the viewpoint that it becomes possible to obtain a cured product mainly composed of the bismaleimide compounds, that photocurability can be improved, and that better heat resistance and thermal stability are obtained.

These bismaleimide compounds (B) may be used singly, or two or more thereof may be appropriately mixed and used.

(Method for Producing Bismaleimide Compound (B))

The bismaleimide compound (B) can be produced by a known method. For example, 1,2,4,5-cyclohexanetetracarboxylic dianhydride, a monomer containing a diamine including a dimer diamine or the like, and maleic anhydride are subjected to a polyaddition reaction at a temperature of normally about 80 to 250° C., preferably about 100 to 200° C. for normally about 0.5 to 50 hours, preferably about 1 to 20 hours to obtain a polyaddition product. The polyaddition product is then subjected to an imidization reaction, i.e. a ring closure reaction with dehydration at a temperature of normally about 60 to 120° C., preferably about 80 to 100° C. for normally about 0.1 to 2 hours, preferably about 0.1 to 0.5 hours to obtain the bismaleimide compound (B).

The dimer diamine can be obtained by, for example, a reductive amination reaction of a dimer acid, and the amination reaction can be conducted by, for example, a known method such as a reduction method using ammonia and a catalyst (e.g. the method described in Japanese Patent Laid-Open No. 9-12712). The dimer acid is a dibasic acid obtained by dimerization of an unsaturated fatty acid through an intermolecular polymerization reaction or the like. Depending on synthesis conditions and purification conditions, a small amount of monomer acids, trimer acids or the like are normally contained in addition to the dimer acid. After the reaction, double bonds remain in the obtained molecule, and in the present embodiment, the dimer acids also include those formed into saturated dibasic acids by reduction of double bonds present in the molecule through a hydrogenation reaction. The dimer acid can be obtained by, for example, polymerizing an unsaturated fatty acid using Lewis acid and Broensted acid as catalysts. The dimer acid can be produced by a known method (e.g. the method described in Japanese Patent Laid-Open No. 9-12712). Examples of the unsaturated fatty acid include crotonic acid, myristoleic acid, palmitoleic acid, oleic acid, elaidic acid, vaccenic acid, gadoleic acid, eicosenoic acid, erucic acid, nervonic acid, linoleic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, Osbond acid, clupanodonic acid, tetracosapentaenoic acid, docosahexaenoic acid and Nisinic acid. The number of carbon atoms in the unsaturated fatty acid is normally 4 to 24, and preferably 14 to 20.

In production of the bismaleimide compound (B), it is preferable that the monomer containing a diamine be dissolved or dispersed in a slurry form in an organic solvent in an inert atmosphere of, for example, argon, nitrogen or the like to form a monomer solution containing a diamine in advance. It is preferable that the 1,2,4,5-cyclohexanetetracarboxylic dianhydride be added to the monomer solution containing a diamine after being dissolved or dispersed in a slurry form in an organic solvent, or in a solid state.

A desired bismaleimide compound (B) can be obtained by adjusting the number of moles of the 1,2,4,5-cyclohexanetetracarboxylic dianhydride and the number of moles of the total amount of the monomer containing a diamine and the maleimide compound.

Various known solvents can be used for the polyaddition reaction and the imidization reaction. Examples of the solvent include amides such as N,N-dimethylformamide, N,N-dimethylacetamide and N-methyl-2-pyrrolidone; ketones such as acetone, methyl ethyl ketone, methyl isobutyl ketone, cyclohexanone and isophorone; esters such as γ-butyrolactone, γ-valerolactone, δ-valerolactone, γ-caprolactone, ε-caprolactone, α-methyl-γ-butyrolactone, ethyl lactate, methyl acetate, ethyl acetate and butyl acetate; aliphatic alcohols having 1 to 10 carbon atoms such as methanol, ethanol and propanol; aromatic group-containing phenols such as phenol and cresol; aromatic group-containing alcohols such as benzyl alcohol; glycols such as ethylene glycol and propylene glycol, monoethers or diethers of these glycols and methanol, ethanol, butanol, hexanol, octanol, benzyl alcohol, phenol, cresol and the like, or glycol ethers such as esters of these monoethers; cyclic ethers such as dioxane and tetrahydrofuran; cyclic carbonates such as ethylene carbonate and propylene carbonate; aliphatic hydrocarbons and aromatic hydrocarbons such as toluene and xylene; and aprotic polar solvents such as dimethylsulfoxide. One of these solvents can be used, or two or more thereof can be combined and used as necessary.

It is preferable to use a catalyst in the imidization reaction. As the catalyst, for example, tertiary amines and dehydration catalysts can be used. The tertiary amine is preferably a heterocyclic tertiary amine, and examples thereof include pyridine, picoline, quinoline and isoquinoline. Examples of the dehydration catalyst include acetic anhydride, propionic anhydride, n-butyric anhydride, benzoic anhydride and trifluoroacetic anhydride.

For the amount of the catalyst added, it is preferable that for example, the amount of an imidizing agent be about 0.5 to 5.0 times the amount of amide groups on a molar basis, and the amount of the dehydration catalyst be 0.5 to 10.0 times the amount of amide groups on a molar basis.

After completion of the imidization reaction, the solution may be used as a bismaleimide compound (B) solution, or a poor solvent may be added to the reaction solvent to form the bismaleimide compound (B) into a solid matter. Examples of the poor solvent include water, methyl alcohol, ethyl alcohol, 2-propyl alcohol, ethylene glycol, triethylene glycol, 2-butyl alcohol, 2-pentyl alcohol, 2-hexyl alcohol, cyclopentyl alcohol, cyclohexyl alcohol, phenol and t-butyl alcohol.

<Maleimide Compound (C)>

The resin composition of the present embodiment preferably further contains a maleimide compound (C) other than the bismaleimide compound (B) according to the present embodiment (also referred to as component (C)). The maleimide compound (C) is at least one selected from the group consisting of a compound represented by formula (8), a compound represented by formula (9), a compound represented by formula (10), a compound represented by formula (11), a compound represented by formula (12), and a compound represented by formula (13). These maleimide compounds (C) may be used singly, or two or more thereof may be appropriately mixed and used. As the maleimide compound (C), a compound represented by formula (8), a compound represented by formula (9), and a compound represented by formula (10) are preferable, and a compound represented by formula (8), and a compound represented by formula (9) are more preferable, from the viewpoint of having a better heat resistance and thermal stability, and exhibiting good solubility in a solvent, a low melting point, low water absorbency, and good compatibility with another resin.

As described above, the reactivity of photo radicals in maleimide compounds is usually very low. However, the bismaleimide compound (B) has superior light transmissivity, as described above. In addition, the compound (A) also has superior light transmissivity, and therefore, by using the compound (A), the maleimide compound (C), and the later-described photo initiator (D), which is blended as necessary, together with the bismaleimide compound (B), light reaches the photo initiator sufficiently, so that the photo radical reaction of the maleimide efficiently takes place, and photocuring can be performed using various active energy rays.

Since the compound (A) and the bismaleimide compound (B) have excellent light transmissivity, light reaches the photo initiator sufficiently, for example, even if an active energy ray including a wavelength of 365 nm or an active energy ray including a wavelength of 405 nm is used, radical reaction using radicals generated from the photo initiator proceeds, and even a composition containing the maleimide compound (C) can be photocured.

Furthermore, the resin composition has excellent alkaline developability and photocurability. Moreover, since the obtained cured product has excellent heat resistance, insulation reliability, and thermal stability, a protective film and an insulation layer can be suitably formed.

Next, the compounds represented by formulas (8) to (13), which are included in the maleimide compound (C), will be described.

(Compound Represented by Formula (8))

The compound represented by the formula (8) is the following compound:

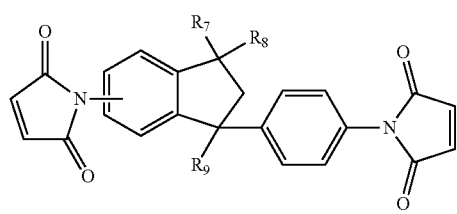

(8)

In the formula (8), $R_7$, $R_8$ and $R_9$ each independently represent a hydrogen atom, or a linear or branched alkyl group having 1 to 8 carbon atoms and optionally having a substituent.

Examples of the linear or branched alkyl group having 1 to 8 carbon atoms and optionally having a substituent include a methyl group, an ethyl group, a propyl group, an isopropyl group, a n-butyl group, an isobutyl group, a tert-butyl group, a n-pentyl group, a 1-ethylpropyl group, a 2,2-dimethylpropyl group, a cyclopentyl group, a hexyl group, and a heptyl group. A hydrogen atom in these alkyl groups may be replaced by a halogen atom such as a fluorine atom or a chlorine atom, a cyano group, or the like. Among these alkyl groups, a methyl group, an ethyl group, an isopropyl group, and a tert-butyl group are preferable, a methyl group, an ethyl group, and an isopropyl group are more preferable, and a methyl group is still more preferable, from the viewpoint of having better photocurability, heat resistance, and thermal stability, and exhibiting good solubility in a solvent, a low melting point, low water absorbency, and good compatibility with another resin.

The compound represented by formula (8) is even more preferably the compound represented by formula (21) (also referred to as TMDM in the present embodiment) from the viewpoint of exhibiting even better photocurability, heat resistance, thermal stability, solubility in a solvent, low melting point, low water absorbency, and compatibility with another resin.

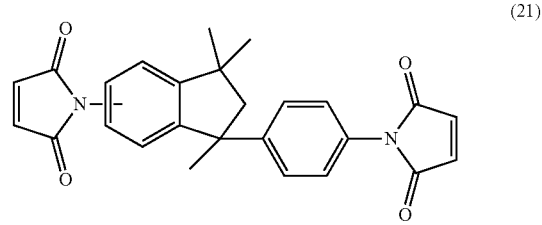

(21)

(Compound Represented by Formula (9))

The compound represented by the formula (9) is the following compound:

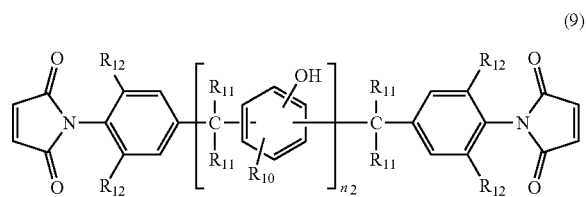

(9)

In formula (9), $R_{10}$, $R_{11}$ and $R_{12}$ each independently represent a hydrogen atom, a hydroxyl group, or a linear or branched alkyl group having 1 to 6 carbon atoms and optionally having a substituent. $n_2$ represents an integer of 1 to 10.

For the linear or branched alkyl group having 1 to 6 carbon atoms, $R_6$ in the above formula (7) can be referred to. As the alkyl group, a methyl group, an ethyl group, an n-propyl group, and an isopropyl group are preferable, and a methyl group is more preferable, from the viewpoint of exhibiting good solubility in a solvent, a low melting point, low water absorbency, and good compatibility with another resin.

For $R_{10}$, $R_{11}$, and $R_{12}$, $R_{10}$ and $R_{12}$ are preferably linear or branched alkyl groups having 1 to 6 carbon atoms, and $R_{11}$ is preferably a hydrogen atom, from the viewpoint of exhibiting better solubility in a solvent. Note that the preferable alkyl groups are as defined above.

$n_2$ is preferably an integer of 1 to 10, and more preferably an integer of 1 to 6 from the viewpoint of having excellent solubility in a solvent, obtaining a more suitable viscosity, and further controlling an increase in the viscosity of the varnish.

As the compound represented by formula (9), a commercial product may be used, and examples thereof include BCPH13 (product name) manufactured by Gunei Chemical Industry Co., Ltd. and represented by formula (22), BCPH01 (product name) manufactured by Gunei Chemical Industry Co., Ltd., and BMCX426 (product name) manufactured by Gunei Chemical Industry Co., Ltd. and represented by formula (23).

(22)

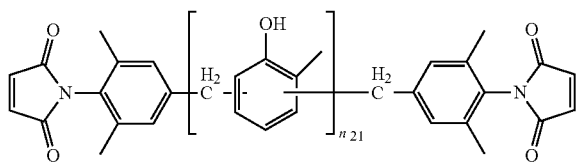

In the formula (22), $n_{21}$ represents an integer of 1 to 5.

(23)

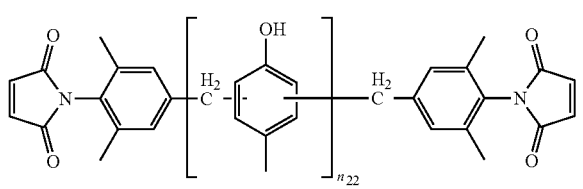

In the formula (23), $n_{22}$ represents an integer of 1 to 10.

(Compound Represented by Formula (10))

The compound represented by the formula (10) is the following compound:

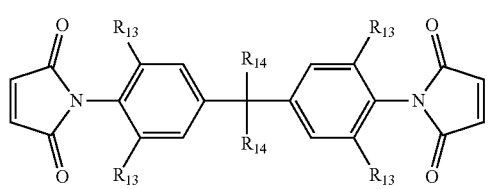
(10)

In the formula (10), each $R_{13}$ independently represents a hydrogen atom, a methyl group, or an ethyl group; and each $R_{14}$ independently represents a hydrogen atom or a methyl group.

$R_{13}$ is preferably a methyl group or an ethyl group, from the viewpoint of exhibiting good solubility in a solvent, a low melting point, low water absorbency, and good compatibility with another resin.

$R_{14}$ is preferably a hydrogen atom, from the viewpoint of exhibiting good solubility in a solvent, a low melting point, low water absorbency, and good compatibility with another resin.

As the maleimide compound represented by the formula (10), commercial products may be used. Examples thereof include BMI-70 (product name) manufactured by K•I Chemical Industry Co., LTD and represented by the formula (24).

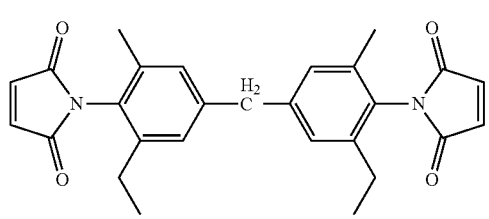
(24)

(Compound Represented by Formula (11))

The compound represented by the formula (11) is the following compound:

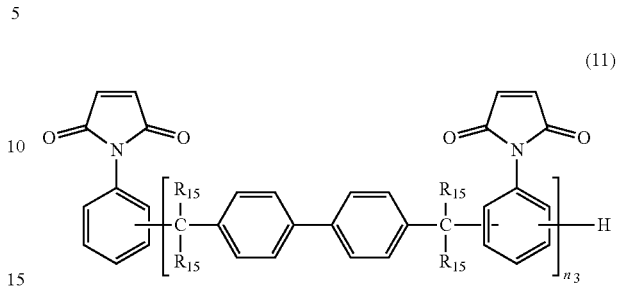
(11)

In the formula (11), each $R_{15}$ independently represents a hydrogen atom or a methyl group. $n_3$ represents an integer of 1 to 10.

As the maleimide compound represented by the formula (11), commercial products may be used. Examples thereof include MIR-3000 (product name) manufactured by Nippon Kayaku Co., Ltd. and represented by the formula (25).

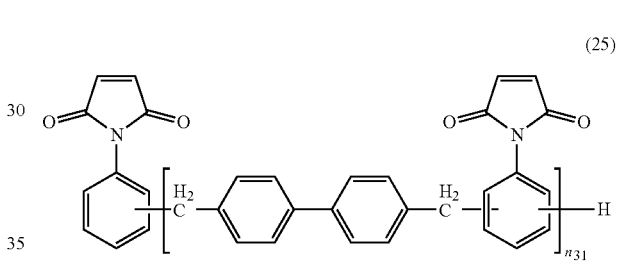
(25)

In the formula (25), $n_{31}$ represents an integer of 1 to 10.

(Compound Represented by Formula (12))

The compound represented by the formula (12) is the following compound:

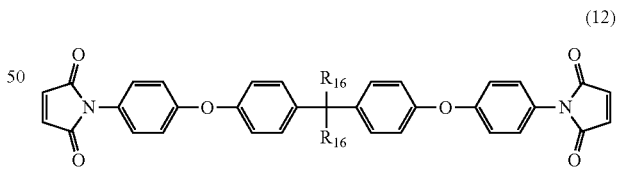
(12)

In the formula (12), each $R_{16}$ independently represents a hydrogen atom, a methyl group, or an ethyl group.

$R_{16}$ is preferably a methyl group or an ethyl group, from the viewpoint of exhibiting good solubility in a solvent, a low melting point, low water absorbency, and good compatibility with another resin.

As the maleimide compound represented by the formula (12), commercial products may be used. Examples thereof include BMI-80 (product name) manufactured by K•I Chemical Industry Co., LTD and represented by the formula (26).

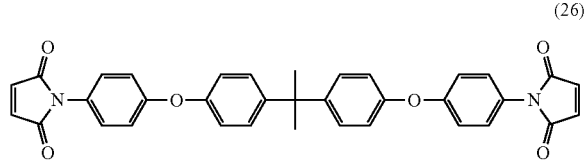 [SMILES: CC(C)(c1ccc(Oc2ccc(N3C(=O)C=CC3=O)cc2)cc1)c1ccc(Oc2ccc(N3C(=O)C=CC3=O)cc2)cc1]

(Compound Represented by Formula (13))

The compound represented by the formula (13) is the following compound:

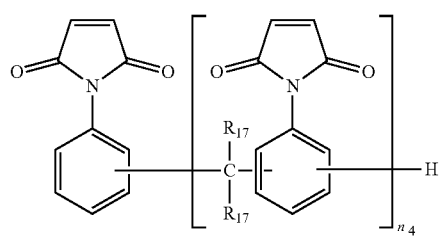

In the formula (13), each $R_{17}$ independently represents a hydrogen atom or a methyl group. $n_4$ represents an integer of 1 to 10.

$R_{17}$ is preferably a hydrogen atom, from the viewpoint of exhibiting good solubility in a solvent, a low melting point, low water absorbency, and good compatibility with another resin.

$n_4$ is more preferably an integer of 1 to 5 from the viewpoint of having excellent solubility in a solvent, obtaining a more suitable viscosity, and further controlling an increase in the viscosity of the varnish.

As the maleimide compound represented by the formula (13), commercial products may be used. Examples thereof include BMI-2300 (product name) manufactured by Daiwa Kasei Industry Co., LTD. and represented by the formula (27).

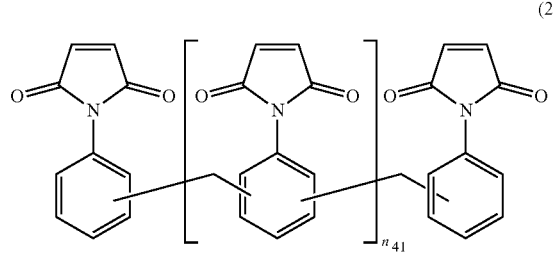

In the formula (27), $n_{41}$ represents an integer of 1 to 5.

In the resin composition, the content of the maleimide compound (C) is preferably 10 to 90 parts by mass, more preferably 20 to 70 parts by mass, and still more preferably 30 to 60 parts by mass in 100 parts by mass of the resin solid content, from the viewpoint that better heat resistance and thermal stability are obtained.

In addition, if the bismaleimide compound (B) and the maleimide compound (C) are contained in the resin composition, the content of the maleimide compound (C) is preferably 10 to 90 parts by mass, more preferably 20 to 70 parts by mass, and still more preferably 30 to 60 parts by mass based on 100 parts by mass of the total of the bismaleimide compound (B) and the maleimide compound (C), from the viewpoint that better heat resistance and thermal stability are obtained.

[Photo Initiator (D)]

The resin composition of the present embodiment preferably further contains a photo initiator (D) (also referred to as component (D)). The photo initiator (D) is not particularly limited, and photo initiators can be used which are publicly known in fields where photo initiators are generally used for photocurable resin compositions. The photo initiator (D) is used together with the compound (A), and the bismaleimide compound (B), the maleimide compound (C), and the like, which are blended as necessary, for photocuring using various active energy rays.

Examples of the photo initiator (D) include radical type photo initiators such as benzoins such as benzoin, benzoin methyl ether, benzoin ethyl ether, benzoin isopropyl ether and benzoin isobutyl ether; organic peroxides exemplified by benzoyl peroxide, lauroyl peroxide, acetyl peroxide, parachlorobenzoyl peroxide, di-tert-butyl-di-perphthalate and the like; phosphine oxides such as 2,4,6-trimethylbenzoyl-diphenyl-phosphine oxide, bis(2,4,6-trimethylbenzoyl)-phenylphosphine oxide, benzoyl-diphenyl-phosphine oxide and bisbenzoyl-phenyphosphine oxide; acetophenones such as acetophenone, 2,2-diethoxy-2-phenylacetophenone, 1,1-dichloroacetophenone, 2-hydroxy-2-methylphenylpropan-1-one, diethoxyacetophenone, 1-hydroxycyclohexylphenylketone, 2-methyl-1-[4-(methylthio)phenyl]-2-morpholino-propan-1-one and 2-benzyl-2-dimethylamino-1-(4-morpholinophenyl)-butanone-1; anthraquinones such as 2-ethylanthraquinone, 2-t-butylanthraquinone, 2-chloroanthraquinone and 2-amylanthraquinone; thioxanthones such as 2,4-diethylthioxanthone, 2-isopropylthioxanthone and 2-chlorothioxanthone; ketals such as acetophenone dimethyl ketal and benzyl dimethyl ketal; benzophenones such as benzophenone, 4-benzoyl-4'-methyldiphenyl sulfide and 4,4'-bismethylaminobenzophenone; and oxime esters such as 1,2-octanedione, 1-[4-(phenylthio)-,2-(O-benzoyloxime)] and ethanone, 1-[9-ethyl-6-(2-methylbenzoyl)-9H-carbazol-3-yl]-,1-(O-acetyloxime);

diazonium salts of Lewis acid such as p-methoxyphenyldiazonium fluorophosphonate and N,N-diethylaminophenyldiazonium hexafluorophosphonate; iodonium salts of Lewis acid such as diphenyliodonium hexafluorophosphonate and diphenyliodonium hexafluoroantimonate; sulfonium salts of Lewis acid such as triphenylsulfonium hexafluorophosphonate and triphenylsulfonium hexafluoroantimonate; phosphonium salts of Lewis acid such as triphenylphosphonium hexafluoroantimonate; additional halides; triazine-based initiators; borate-based initiators; and cationic photo initiators such as additional photoacid generators.

As the photo initiator (D), commercial products can also be used. Examples thereof include Omnirad (registered trademark) 369 (product name) manufactured by IGM Resins B.V., Omnirad (registered trademark) 819 (product name) manufactured by IGM Resins B.V., Omnirad (registered trademark) 819DW (product name) manufactured by IGM Resins B.V., Omnirad (registered trademark) 907 (product name) manufactured by IGM Resins B.V., Omnirad (registered trademark) TPO (product name) manufactured by IGM Resins B.V., Omnirad (registered trademark) TPO-G (product name) manufactured by IGM Resins B.V., Omnirad (registered trademark) 784 (product name) manufactured by IGM Resins B.V., Irgacure (registered trademark) OXE01 (product name) manufactured by BASF Japan Ltd., Irgacure (registered trademark) OXE02 (product name) manufactured by BASF Japan Ltd., Irgacure (registered trademark) OXE03 (product name) manufactured by BASF Japan Ltd., and Irgacure (registered trademark) OXE04 (product name) manufactured by BASF Japan Ltd.

These photo initiators (D) may be used singly, or two or more thereof may be appropriately mixed and used.

The photo initiator (D) has an absorbance of preferably 0.1 or more when a chloroform solution containing the photo initiator (D) at 0.01% by mass is prepared, and the absorbance of the chloroform solution containing the photo initiator (D) at 0.01% by mass is measured using an active energy ray including a wavelength of 365 nm (i-line). In this case, the photo initiator (D) exhibits outstanding light absorption. In addition, the photo initiator (D) has an absorbance of preferably 0.1 or more when the absorbance of a chloroform solution containing the photo initiator (D) at 0.01% by mass is measured using an active energy ray including a wavelength of 405 nm (h-line). Even in this case, superior light absorption is exhibited. When such a photo initiator (D) is used, for example, upon producing a printed wiring board having a highly dense and highly detailed wiring formation (pattern) using the direct imaging method, the photo radical reaction of the maleimide occurs efficiently even when an active energy ray including a wavelength of 405 nm (h-line) is used. The absorbance at a wavelength of 365 nm (i-line) is more preferably 0.15 or more because a resin composition that is superior in photocurability can be obtained. The absorbance at a wavelength of 405 nm (h-line) is more preferably 0.15 or more because a resin composition that is superior in photocurability can be obtained. The upper limit of each of the absorbance at a wavelength of 365 nm (i-line) and the absorbance at a wavelength of 405 nm (h-line) is, for example, 99.9 or less.

As such a photo initiator (D), a compound represented by the formula (14) is preferable.

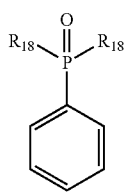

(14)

In the formula (14), each $R_{18}$ independently represents a substituent represented by the formula (15) or a phenyl group.

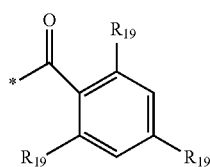

(15)

In the formula (15), each $R_{19}$ independently represents a hydrogen atom or a methyl group. In the formula (15), -* indicates a bonding hand to a phosphorus atom (P) directly bonded to $R_{18}$ in the formula (14).

As for the compound represented by the formula (14), when a chloroform solution containing this compound at 0.01% by mass is prepared and the absorbance of this chloroform solution is measured using an active energy ray including a wavelength of 365 nm (i-line), the absorbance is 0.1 or more, exhibiting superior absorption of the light with a wavelength of 365 nm (i-line). Therefore, this compound suitably generates radicals in response to the light with a wavelength of 365 nm (i-line). The absorbance is preferably 0.15 or more. The upper limit value is, for example, 10.0 or less, and may be 5.0 or less, or 2.0 or less.

As for the compound represented by the formula (14), when a chloroform solution containing this compound at 0.01% by mass is prepared and the absorbance of this chloroform solution is measured using an active energy ray including a wavelength of 405 nm (h-line), the absorbance is 0.1 or more, exhibiting superior absorption of the light with a wavelength of 405 nm (h-line). Therefore, this compound suitably generates radicals in response to the light with a wavelength of 405 nm (h-line). The absorbance is more preferably 0.15 or more. The upper limit value is, for example, 10.0 or less, and may be 5.0 or less, or 2.0 or less.

In the formula (14), each $R_{18}$ independently represents a substituent represented by the formula (15) or a phenyl group. It is preferable that one or more among $R_{18}$s be the substituents represented by the formula (15).

In the formula (15), each $R_{19}$ independently represents a hydrogen atom or a methyl group. It is preferable that one or more among $R_{19}$s be methyl groups, and it is more preferable that all should be methyl groups.

Examples of the compound represented by the formula (14) include acylphosphine oxides such as 2,4,6-trimethyl-benzoyl-diphenyl-phosphine oxide and bis(2,4,6-trimethyl-benzoyl)-phenylphosphine oxide. Among the above, bis(2, 4,6-trimethylbenzoyl)-phenylphosphine oxide is preferable because it has excellent light transmissivity. These compounds may be used singly, or two or more thereof may be appropriately mixed and used.

Acylphosphine oxides exhibit superior absorption of an active energy ray including a wavelength of 405 nm (h-line) and can suitably radical polymerize the bismaleimide compound (B) and the maleimide compound (C) at a wavelength of 405 nm (h-line), for example. Therefore, according to the present embodiment, it is possible to suitably produce a resin composition which does not hinder photocuring reaction and has excellent photocurability in an exposure step and is capable of imparting excellent alkaline developability in a development step when used for a multilayer printed wiring board; and a resin sheet, a multilayer printed wiring board and a semiconductor device obtained using the resin composition.

In the resin composition, the content of the photo initiator (D) is preferably 0.1 to 50 parts by mass, more preferably 0.2 to 30 parts by mass, and still more preferably 0.3 to 10 parts by mass based on 100 parts by mass of the resin solid content from the viewpoint that photocuring sufficiently proceeds without inhibiting the photocuring reaction in the resin composition and the exposed portion is sufficiently insolubilized in alkaline developability.

In addition, if the bismaleimide compound (B) and the maleimide compound (C) are contained in the resin composition, the content of the photo initiator (D) is preferably 0.1 to 50 parts by mass, more preferably 0.2 to 30 parts by mass, and still more preferably 0.3 to 10 parts by mass based on 100 parts by mass of the total of the bismaleimide compound (B) and the maleimide compound (C) from the viewpoint that photocuring sufficiently proceeds without inhibiting the photocuring reaction in the resin composition and the exposed portion is sufficiently insolubilized in alkaline developability.

[Maleimide Compound (E) Other than Bismaleimide Compound (B) and Maleimide Compound (C)]

In the resin composition of the present embodiment, a maleimide compound (E) other than the bismaleimide compound (B) and the maleimide compound (C) (also referred to as component (E)) can be used as long as the effect of the present invention is achieved. As described above, the compound (A) and the bismaleimide compound (B) have superior light transmissivity, so that even when the maleimide compound (E) is used, light reaches the photo initiator sufficiently, the photo radical reaction of the maleimide efficiently takes place, and photocuring can be performed using various active energy rays. Therefore, light reaches the photo initiator sufficiently, for example, even when an active energy ray including a wavelength of 365 nm or an active energy ray including a wavelength of 405 nm is used, radical reaction using radicals generated from the photo initiator proceeds, and even a composition containing the maleimide compound (E) can be photocured.

The maleimide compound (E) is not particularly limited as long as it is a compound other than the bismaleimide compound (B) and the maleimide compound (C) and has one or more maleimide groups in the molecule. Examples thereof include N-phenylmaleimide, N-cyclohexylmaleimide, N-hydroxyphenylmaleimide, N-anilinophenylmaleimide, N-carboxyphenylmaleimide, N-(4-carboxy-3-hydroxyphenyl)maleimide, 6-maleimidohexanoic acid, 4-maleimidobutyric acid, bis(4-maleimidophenyl)methane, 2,2-bis{4-(4-maleimidophenoxy)-phenyl}propane, 4,4-diphenylmethanebismaleimide, bis(3,5-dimethyl-4-maleimidophenyl)methane, bis(3-ethyl-5-methyl-4-maleimidophenyl)methane, bis(3,5-diethyl-4-maleimidophenyl)methane, phenylmethanemaleimide, o-phenylenebismaleimide, m-phenylenebismaleimide, p-phenylenebismaleimide, o-phenylenebiscitraconimide, m-phenylenebiscitraconimide, p-phenylenebiscitraconimide, 2,2-bis(4-(4-maleimidophenoxy)-phenyl)propane, 3,3-dimethyl-5,5-diethyl-4,4-diphenylmethanebismaleimide, 4-methyl-1,3-phenylenebismaleimide, 1,2-bis(maleimido)ethane, 1,4-bis(maleimido)butane, 1,5-bis(maleimido)pentane, 1,5-bismaleimido-2-methylpentane, 1,6-bis(maleimido)hexane, 1,6-bismaleimido-(2,2,4-trimethyl)hexane, 1,8-bismaleimido-3,6-dioxaoctane, 1,11-bismaleimido-3,6,9-trioxaundecane, 1,3-bis(maleimidomethyl)cyclohexane, 1,4-bis(maleimidomethyl)cyclohexane, 4,4-diphenyl ether bismaleimide, 4,4-diphenyl sulfone bismaleimide, 1,3-bis(3-maleimidophenoxy)benzene, 1,3-bis(4-maleimidophenoxy)benzene, 4,4-diphenylmethanebiscitraconimide, 2,2-bis[4-(4-citraconimidophenoxy)phenyl]propane, bis(3,5-dimethyl-4-citraconimidophenyl)methane, bis(3-ethyl-5-methyl-4-citraconimidophenyl)methane, bis(3,5-diethyl-4-citraconimidophenyl)methane, polyphenylmethanemaleimide, fluorescein-5-maleimide, as well as a prepolymer of these maleimide compounds, or a prepolymer of maleimide compounds and amine compounds. These maleimide compounds (E) may be used singly, or two or more thereof may be appropriately mixed and used.

If the bismaleimide compound (B) and the maleimide compound (C) are contained in the resin composition, the content of the maleimide compound (E) is preferably 1 to 50 parts by mass, more preferably 1 to 40 parts by mass, and still more preferably 1 to 30 parts by mass based on 100 parts by mass of the total of the bismaleimide compound (B) and the maleimide compound (C), from the viewpoint of exhibiting excellent photocurability.

[Filler (F)]

In the resin composition of the present embodiment, a filler (F) (also referred to as component (F)) can be used for improving a variety of characteristics such as a coating property and heat resistance. The filler (F) is preferably one that has an insulation property and does not inhibit transmissivity for various active energy rays used for photocuring, and more preferably one that does not inhibit transmissivity for active energy rays including a wavelength of 365 nm (i-line) and/or a wavelength of 405 nm (h-line).

Examples of the filler (F) include silica (for example, natural silica, fused silica, amorphous silica and hollow silica), an aluminum compound (for example, boehmite, aluminum hydroxide, alumina and aluminum nitride), a boron compound (for example, boron nitride), a magnesium compound (for example, magnesium oxide and magnesium hydroxide), a calcium compound (for example, calcium carbonate), a molybdenum compound (for example, molybdenum oxide and zinc molybdate), a barium compound (for example, barium sulfate and barium silicate), talc (for example, natural talc and calcined talc), mica, glass (for example, short fibrous glass, spherical glass, fine powder glass, E glass, T glass and D glass), silicone powder, a fluororesin-based filler, a urethane resin-based filler, a (meth)acrylic resin-based filler, a polyethylene-based filler, a styrene-butadiene rubber, and a silicone rubber. These fillers (F) may be used singly, or two or more thereof may be appropriately mixed and used.

Among the above, it is preferable that the filler (F) should be one or more selected from the group consisting of silica, boehmite, barium sulfate, silicone powder, a fluororesin-based filler, a urethane resin-based filler, a (meth)acrylic resin-based filler, a polyethylene-based filler, a styrene-butadiene rubber, and a silicone rubber.

These fillers (F) may be surface-treated with a silane coupling agent, which will be mentioned later, or the like.

From the viewpoint of improving the heat resistance of the cured product and also obtaining a good coating property, silica is preferable and fused silica is more preferable. Specific examples of the silica include SFP-130MC (product name) manufactured by Denka Company Limited, and SC2050-MB (product name), SC1050-MLE (product name), YA010C-MFN (product name), and YA050C-MJA (product name) manufactured by Admatechs Company Limited.

The particle diameter of the filler (F) is not particularly limited, but from the viewpoint of ultraviolet light transmissivity of the resin composition, it is normally 0.005 to 10 μm, and is preferably 0.01 to 1.0 μm.

In the resin composition, the content of the filler (F) is normally preferably 300 parts by mass or less, more preferably 200 parts by mass or less, and still more preferably 100 parts by mass or less based on 100 parts by mass of the resin solid content in the resin composition, from the viewpoint of improving the ultraviolet light transmissivity of the resin composition and the heat resistance of the cured product. When a filler is contained, the lower limit value of its content is normally 1 part by mass based on 100 parts by mass of the resin solid content in the resin composition from the viewpoint of obtaining effects of improving a variety of characteristics such as a coating property and heat resistance.

[Silane Coupling Agent and Wetting and Dispersing Agent]

In the resin composition of the present embodiment, a silane coupling agent and/or a wetting and dispersing agent can also be used in combination in order to improve the dispersibility of the filler, and the adhesive strength between the polymers and/or the resins and the filler.

The silane coupling agent is not particularly limited as long as it is a silane coupling agent generally used for surface treatment of inorganic matters. Examples thereof include aminosilane-based compounds such as 3-aminopropyltrimethoxysilane, γ-aminopropyltriethoxysilane, 3-aminopropyldimethoxymethylsilane, 3-aminopropyldiethoxymethylsilane, N-β-(aminoethyl)-γ-aminopropyltrimethoxysilane, N-(2-aminoethyl)-3-aminopropyltriethoxysilane, N-(2-aminoethyl)-3-aminopropyldimethoxymethylsilane, N-(2-aminoethyl)-3-aminopropyldiethoxymethylsilane, N-phenyl-3-aminopropyltrimethoxysilane, N-phenyl-3-aminopropyltriethoxysilane, [3-(6-aminohexylamino)propyl]trimethoxysilane and [3-(N,N-dimethylamino)propyl]trimethoxysilane; epoxysilane-based compounds such as γ-glycidoxypropyltrimethoxysilane, 3-glycidoxypropyltriethoxysilane, 3-glycidoxypropyldimethoxymethylsilane, 3-glycidoxypropyldiethoxymethylsilane, 2-(3,4-epoxycyclohexyl)ethyltrimethoxysilane and [8-(glycidyloxy)-n-octyl]trimethoxysilane; vinylsilane-based compounds such as vinyltris(2-methoxyethoxy)silane, vinyltrimethoxysilane, vinyltriethoxysilane, dimethoxymethylvinylsilane, diethoxymethylvinylsilane, trimethoxy(7-octen-1-yl)silane and trimethoxy(4-vinylphenyl)silane; methacrylic silane-based compounds such as 3-methacryloxypropyltrimethoxysilane, 3-methacryloxypropyltriethoxysilane, 3-methacryloxypropyldimethoxymethylsilane and 3-methacryloxypropyldiethoxymethylsilane; acrylic silane-based compounds such as 3-acryloxypropyltrimethoxysilane and 3-acryloxypropyltriethoxysilane; isocyanate silane-based compounds such as 3-isocyanatepropyltrimethoxysilane and 3-isocyanatepropyltriethoxysilane; isocyanurate silane-based compounds such as tris-(trimethoxysilylpropyl)isocyanurate; mercaptosilane-based compounds such as 3-mercaptopropyltrimethoxysilane and 3-mercaptopropyldimethoxymethylsilane; ureidosilane-based compounds such as 3-ureidopropyltriethoxysilane; styrylsilane-based compounds such as p-styryltrimethoxysilane; cationic silane-based compounds such as N-β-(N-vinylbenzylaminoethyl)-γ-aminopropyltrimethoxysilane hydrochlorides; acid anhydride-based compounds such as [3-(trimethoxysilyl)propyl]succinic anhydride; phenylsilane-based compounds such as phenyltrimethoxysilane, phenyltriethoxysilane, dimethoxymethylphenylsilane, diethoxymethylphenylsilane and p-tolyltrimethoxysilane; and arylsilane-based compounds such as trimethoxy(l-naphthyl)silane. These silane coupling agents may be used singly, or two or more thereof may be appropriately mixed and used.

In the resin composition, the content of the silane coupling agent is normally 0.1 to 10 parts by mass based on 100 parts by mass of the resin solid content in the resin composition.

The wetting and dispersing agent is not particularly limited as long as it is a dispersion stabilizer used for a paint. Specific examples thereof include DISPERBYK (registered trademark)-110 (product name), 111 (product name), 118 (product name), 180 (product name), and 161 (product name), BYK (registered trademark)-W996 (product name), W9010 (product name), and W903 (product name) manufactured by BYK Japan KK. These wetting and dispersing agents may be used singly, or two or more thereof may be appropriately mixed and used.

In the resin composition, the content of the wetting and dispersing agent is normally 0.1 to 10 parts by mass based on 100 parts by mass of the resin solid content in the resin composition.

[Cyanate Compound, Phenolic Resin, Oxetane Resin, Benzoxazine Compound, Epoxy Resin, and Additional Compound]

In the present embodiment, as long as the effect of the present invention is achieved, a variety of types of compounds and resins can be used, such as a cyanate compound, a phenolic resin, an oxetane resin, a benzoxazine compound, epoxy resin and additional compounds in addition to the compound (A), the bismaleimide compound (B), the maleimide compound (C), the photo initiator (D) and the maleimide compound (E), depending on properties such as flame retardancy, heat resistance and a thermal expansion property of the cured product. Preferably, these compounds and resins ensure that the resin composition becomes light-sensitive to be photocured when exposed with an active energy ray including a wavelength of 365 nm (i-line) and/or an active energy ray including a wavelength of 405 nm (h-line).

These compounds and resins may be used singly, or two or more thereof may be appropriately mixed and used.

<Cyanate Compound>

The cyanate compound is not particularly limited as long as it is a resin having in the molecule an aromatic moiety substituted by at least one cyanate group (cyanate group).

For example, mention may be made of those represented by the formula (28).

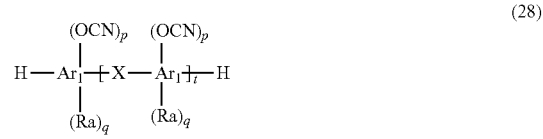

(28)

In the formula (28), $Ar_1$ represents a benzene ring, a naphthalene ring, or two benzene rings bonded to each other by a single bond. When there are a plurality of $Ar_1$, $Ar_1$ may be the same as or different from each other. Each Ra independently represents a hydrogen atom, an alkyl group having 1 to 6 carbon atoms, an alkenyl group having 2 to 6 carbon atoms, an aryl group having 6 to 12 carbon atoms, an alkoxyl group having 1 to 4 carbon atoms, or a group in which an alkyl group having 1 to 6 carbon atoms and an aryl group having 6 to 12 carbon atoms are bonded to each other. The aromatic ring for Ra may have a substituent, and any position can be selected for the substituents in $Ar_1$ and Ra. p represents the number of cyanate groups bonded to $Ar_1$ and is each independently an integer of 1 to 3. q represents the number of Ra bonded to $Ar_1$ and is 4-p when $Ar_1$ is a benzene ring, 6-p when $Ar_1$ is a naphthalene ring, and 8-p when $Ar_1$ is two benzene rings bonded to each other by a single bond. t represents the average number of repetitions and is an integer of 0 to 50, and the cyanate compound may be a mixture of compounds having different t. X represents any of a single bond, a divalent organic group having 1 to 50 carbon atoms (a hydrogen atom may be replaced by a heteroatom), a divalent organic group having 1 to 10 nitrogen atoms (for example, —N—R—N—, wherein R represents an organic group), a carbonyl group (—CO—), a carboxy group (—C(=O)O—), a carbonyl dioxide group (—OC(=O)O—), a sulfonyl group (—SO$_2$—), a divalent sulfur atom, and a divalent oxygen atom, and X is each independently as defined above when there are a plurality of X.

The alkyl group for Ra in the formula (28) may have either a linear or branched chain structure or a cyclic structure (for example, a cycloalkyl group).

In addition, a hydrogen atom in the alkyl group and the aryl group for Ra in the formula (28) may be replaced by a halogen atom such as a fluorine atom and a chlorine atom; an alkoxyl group such as a methoxy group and a phenoxy group; a cyano group, or the like.

Specific examples of the alkyl group include a methyl group, an ethyl group, a propyl group, an isopropyl group, a n-butyl group, an isobutyl group, a tert-butyl group, a n-pentyl group, a 1-ethylpropyl group, a 2,2-dimethylpropyl group, a cyclopentyl group, a hexyl group, a cyclohexyl group, and a trifluoromethyl group.

Specific examples of the alkenyl group include a vinyl group, a (meth)allyl group, an isopropenyl group, a 1-propenyl group, a 2-butenyl group, a 3-butenyl group, a 1,3-butanedienyl group, 2-methyl-2-propenyl group, a 2-pentenyl group, and a 2-hexenyl group.

Specific examples of the aryl group include a phenyl group, a xylyl group, a mesityl group, a naphthyl group, a phenoxyphenyl group, an ethylphenyl group, an o-, m-, or p-fluorophenyl group, a dichlorophenyl group, a dicyanophenyl group, a trifluorophenyl group, a methoxyphenyl group, and an o-, m-, or p-tolyl group.

Examples of the alkoxyl group include a methoxy group, an ethoxy group, a propoxy group, an isopropoxy group, a n-butoxy group, an isobutoxy group, and a tert-butoxy group.

Specific examples of the divalent organic group having 1 to 50 carbon atoms for X in the formula (28) include a methylene group, an ethylene group, a trimethylene group, a cyclopentylene group, a cyclohexylene group, a trimethylcyclohexylene group, a biphenylylmethylene group, a dimethylmethylene-phenylene-dimethylmethylene group, a fluorenediyl group, and a phthalidediyl group. A hydrogen atom in the divalent organic group may be replaced by a halogen atom such as a fluorine atom and a chlorine atom; an alkoxyl group such as a methoxy group and a phenoxy group; a cyano group, or the like.

Examples of the divalent organic group having 1 to 10 nitrogen atoms for X in the formula (28) include an imino group and a polyimide group.

In addition, examples of the organic group of X in the formula (28) include one having a structure represented by the formula (29), or one having a structure represented by the formula (30).

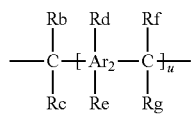

(29)

In the formula (29), $Ar_2$ represents a benzenediyl group, a naphthalenediyl group, or a biphenyldiyl group, and may be the same as or different from each other when u is an integer of 2 or more. Rb, Rc, Rf, and Rg each independently represent a hydrogen atom, an alkyl group having 1 to 6 carbon atoms, an aryl group having 6 to 12 carbon atoms, a trifluoromethyl group, or an aryl group having at least one phenolic hydroxy group. Rd and Re are each independently selected from any one of a hydrogen atom, an alkyl group having 1 to 6 carbon atoms, an aryl group having 6 to 12 carbon atoms, an alkoxyl group having 1 to 4 carbon atoms, and a hydroxy group. u represents an integer of 0 to 5.

(30)

In the formula (30), $Ar_a$ represents a benzenediyl group, a naphthalenediyl group, or a biphenyldiyl group, and may be the same as or different from each other when v is an integer of 2 or more. Ri and Rj each independently represent a hydrogen atom, an alkyl group having 1 to 6 carbon atoms, an aryl group having 6 to 12 carbon atoms, a benzyl group, an alkoxyl group having 1 to 4 carbon atoms, a hydroxy group, a trifluoromethyl group, or an aryl group substituted by at least one cyanate group. v represents an integer of 0 to 5, and the cyanate compound may be a mixture of compounds having different v.

Furthermore, examples of X in the formula (28) include divalent groups represented by the following formulas.

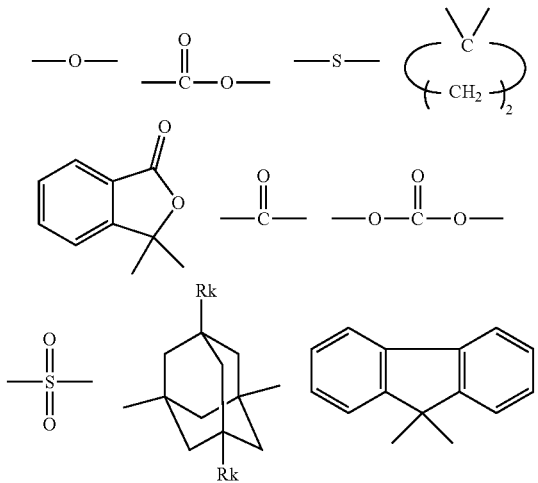

Here, in the above formula, z represents an integer of 4 to 7. Each Rk independently represents a hydrogen atom or an alkyl group having 1 to 6 carbon atoms.

Specific examples of $Ar_2$ in the formula (29) and $Ar_3$ in the formula (30) include a benzenediyl group to which two carbon atoms shown in the formula (29) or two oxygen atoms shown in the formula (30) are bonded at positions 1 and 4 or positions 1 and 3, a biphenyldiyl group to which the above two carbon atoms or two oxygen atoms are bonded at positions 4 and 4', positions 2 and 4', positions 2 and 2', positions 2 and 3', positions 3 and 3', or positions 3 and 4', and a naphthalenediyl group to which the above two carbon atoms or two oxygen atoms are bonded at positions 2 and 6, positions 1 and 5, positions 1 and 6, positions 1 and 8, positions 1 and 3, positions 1 and 4, or positions 2 and 7.

The alkyl group and the aryl group for Rb, Rc, Rd, Re, Rf, and Rg in the formula (29) and Ri and Rj in the formula (30) have the same meanings as those in the above formula (28).

Specific examples of the cyanato-substituted aromatic compound represented by the formula (28) include cyanatobenzene, 1-cyanato-2-, 1-cyanato-3-, or 1-cyanato-4-methylbenzene, 1-cyanato-2-, 1-cyanato-3-, or 1-cyanato-4-methoxybenzene, 1-cyanato-2,3-, 1-cyanato-2,4-, 1-cyanato-2,5-, 1-cyanato-2,6-, 1-cyanato-3,4-, or 1-cyanato-3,5-dimethylbenzene, cyanatoethylbenzene, cyanatobutylbenzene, cyanatooctylbenzene, cyanatononylbenzene, 2-(4-cyanatophenyl)-2-phenylpropane (a cyanate of 4-α-cumylphenol), 1-cyanato-4-cyclohexylbenzene, 1-cyanato-4-vinylbenzene, 1-cyanato-2- or 1-cyanato-3-chlorobenzene, 1-cyanato-2,6-dichlorobenzene, 1-cyanato-2-methyl-3-chlorobenzene, cyanatonitrobenzene, 1-cyanato-4-nitro-2-ethylbenzene, 1-cyanato-2-methoxy-4-allylbenzene (a cyanate of eugenol), methyl(4-cyanatophenyl)sulfide, 1-cyanato-3-trifluoromethylbenzene, 4-cyanatobiphenyl, 1-cyanato-2- or 1-cyanato-4-acetylbenzene, 4-cyanatobenzaldehyde, methyl 4-cyanatobenzoate ester, phenyl 4-cyanatobenzoate ester, 1-cyanato-4-acetaminobenzene, 4-cyanatobenzophenone, 1-cyanato-2,6-di-tert-butylbenzene, 1,2-dicyanatobenzene, 1,3-dicyanatobenzene, 1,4-dicyanatobenzene, 1,4-dicyanato-2-tert-butylbenzene, 1,4-dicyanato-2,4-dimethylbenzene, 1,4-dicyanato-2,3,4-dimethylbenzene, 1,3-dicyanato-2,4,6-trimethylbenzene, 1,3-dicyanato-5-methylbenzene, 1-cyanato- or 2-cyanatonaphthalene, 1-cyanato-4-methoxynaphthalene, 2-cyanato-6-methoxynaphthalene, 2-cyanato-7-methoxynaphthalene, 2,2'-dicyanato-1,1'-binaphthyl, 1,3-, 1,4-, 1,5-, 1,6-, 1,7-, 2,3-, 2,6-, or 2,7-dicyanatonaphthalene, 2,2'- or 4,4'-dicyanatobiphenyl, 4,4'-dicyanatooctafluorobiphenyl, 2,4'- or 4,4'-dicyanatodiphenylmethane, bis(4-cyanato-3,5-dimethylphenyl)methane, 1,1-bis(4-cyanatophenyl)ethane, 1,1-bis(4-cyanatophenyl)propane, 2,2-bis(4-cyanatophenyl)propane, 2,2-bis(4-cyanato-3-methylphenyl)propane, 2,2-bis(2-cyanato-5-biphenylyl)propane, 2,2-bis(4-cyanatophenyl) hexafluoropropane, 2,2-bis(4-cyanato-3,5-dimethylphenyl)propane, 1,1-bis(4-cyanatophenyl)butane, 1,1-bis(4-cyanatophenyl)isobutane, 1,1-bis(4-cyanatophenyl)pentane, 1,1-bis(4-cyanatophenyl)-3-methylbutane, 1,1-bis(4-cyanatophenyl)-2-methylbutane, 1,1-bis(4-cyanatophenyl)-2,2-dimethylpropane, 2,2-bis(4-cyanatophenyl)butane, 2,2-bis(4-cyanatophenyl)pentane, 2,2-bis(4-cyanatophenyl)hexane, 2,2-bis(4-cyanatophenyl)-3-methylbutane, 2,2-bis(4-cyanatophenyl)-4-methylpentane, 2,2-bis(4-cyanatophenyl)-3,3-dimethylbutane, 3,3-bis(4-cyanatophenyl)hexane, 3,3-bis(4-cyanatophenyl)heptane, 3,3-bis(4-cyanatophenyl)octane, 3,3-bis(4-cyanatophenyl)-2-methylpentane, 3,3-bis(4-cyanatophenyl)-2-methylhexane, 3,3-bis(4-cyanatophenyl)-2,2-dimethylpentane, 4,4-bis(4-cyanatophenyl)-3-methylheptane, 3,3-bis(4-cyanatophenyl)-2-methylheptane, 3,3-bis(4-cyanatophenyl)-2,2-dimethylhexane, 3,3-bis(4-cyanatophenyl)-2,4-dimethylhexane, 3,3-bis(4-cyanatophenyl)-2,2,4-trimethylpentane, 2,2-bis(4-cyanatophenyl)-1,1,1,3,3,3-hexafluoropropane, bis(4-cyanatophenyl)phenylmethane, 1,1-bis(4-cyanatophenyl)-1-phenylethane, bis(4-cyanatophenyl)biphenylmethane, 1,1-bis(4-cyanatophenyl)cyclopentane, 1,1-bis(4-cyanatophenyl)cyclohexane, 2,2-bis(4-cyanato-3-isopropylphenyl)propane, 1,1-bis(3-cyclohexyl-4-cyanatophenyl)cyclohexane, bis(4-cyanatophenyl) diphenylmethane, bis(4-cyanatophenyl)-2,2-dichloroethylene, 1,3-bis[2-(4-cyanatophenyl)-2-propyl] benzene, 1,4-bis[2-(4-cyanatophenyl)-2-propyl]benzene, 1,1-bis(4-cyanatophenyl)-3,3,5-trimethylcyclohexane, 4-[bis(4-cyanatophenyl)methyl]biphenyl, 4,4-dicyanatobenzophenone, 1,3-bis(4-cyanatophenyl)-2-propen-1-one, bis (4-cyanatophenyl) ether, bis(4-cyanatophenyl) sulfide, bis (4-cyanatophenyl) sulfone, 4-cyanatobenzoic acid-4-cyanatophenyl ester (4-cyanatophenyl-4-cyanatobenzoate), bis-(4-cyanatophenyl) carbonate, 1,3-bis(4-cyanatophenyl) adamantane, 1,3-bis(4-cyanatophenyl)-5,7-dimethyladamantane, 3,3-bis(4-cyanatophenyl)isobenzofuran-1(3H)-one (a cyanate of phenolphthalein), 3,3-bis(4-cyanato-3-methylphenyl)isobenzofuran-1(3H)-one (a cyanate of o-cresolphthalein), 9,9'-bis(4-cyanatophenyl)fluorene, 9,9-bis(4-cyanato-3-methylphenyl)fluorene, 9,9-bis(2-cyanato-5-biphenylyl)fluorene, tris(4-cyanatophenyl)methane, 1,1,1-tris(4-cyanatophenyl)ethane, 1,1,3-tris(4-cyanatophenyl) propane, α,α,α'-tris(4-cyanatophenyl)-1-ethyl-4-isopropylbenzene, 1,1,2,2-tetrakis(4-cyanatophenyl)ethane, tetrakis(4-cyanatophenyl)methane, 2,4,6-tris(N-methyl-4-cyanatoanilino)-1,3,5-triazine, 2,4-bis(N-methyl-4-cyanatoanilino)-6-(N-methylanilino)-1,3,5-triazine, bis(N-4-cyanato-2-methylphenyl)-4,4'-oxydiphthalimide, bis(N-3-cyanato-4-methylphenyl)-4,4'-oxydiphthalimide, bis(N-4-cyanatophenyl)-4,4'-oxydiphthalimide, bis(N-4-cyanato-2-methylphenyl)-4,4'-(hexafluoroisopropylidene) diphthalimide, tris(3,5-dimethyl-4-cyanatobenzyl) isocyanurate, 2-phenyl-3,3-bis(4-cyanatophenyl)phthalimidine, 2-(4-methylphenyl)-3,3-bis(4-cyanatophenyl)phthalimidine, 2-phenyl-3,3-bis(4-cyanato-3-methylphenyl) phthalimidine, 1-methyl-3,3-bis(4-cyanatophenyl)indolin-2-one, and 2-phenyl-3,3-bis(4-cyanatophenyl)indolin-2-one.

These cyanate compounds may be used singly, or two or more thereof may be appropriately mixed and used.

Other specific examples of the cyanate compound represented by the formula (28) include those obtained by cyanation of a phenolic resin such as a phenol novolac resin and a cresol novolac resin (those obtained by reacting phenol, an alkyl-substituted phenol or a halogen-substituted phenol with a formaldehyde compound such as formalin or paraformaldehyde in an acidic solution, using a publicly known method), a trisphenol novolac resin (those obtained by reacting hydroxybenzaldehyde with phenol in the presence of an acidic catalyst), a fluorene novolac resin (those obtained by reacting a fluorenone compound with a 9,9-bis (hydroxyaryl)fluorene in the presence of an acidic catalyst), a phenol aralkyl resin, a cresol aralkyl resin, a naphthol aralkyl resin, and a biphenyl aralkyl resin (those obtained by reacting a bishalogenomethyl compound as represented by $Ar_4$—$(CH_2Y)_2$ (wherein $Ar_4$ represents a phenyl group and Y represents a halogen atom. The same applies in this paragraph) with a phenolic compound with an acidic catalyst or with no catalyst, those obtained by reacting a bis (alkoxymethyl) compound as represented by $Ar_4$—$(CH_2OR)_2$ (wherein R represents an alkyl group) with a phenolic compound in the presence of an acidic catalyst, or those obtained by reacting a bis(hydroxymethyl) compound as represented by $Ar_4$—$(CH_2OH)_2$ with a phenolic compound in the presence of an acidic catalyst, or those obtained by polycondensing an aromatic aldehyde compound, an aralkyl compound, and a phenolic compound, using a publicly known method), a phenol-modified xylene formaldehyde resin (those obtained by reacting a xylene formaldehyde resin with a phenolic compound in the presence of an acidic catalyst, using a publicly known method), a modified naphthalene formaldehyde resin (those obtained by reacting a naphthalene formaldehyde resin with a hydroxy-substituted aromatic compound in the presence of an acidic catalyst, using a publicly known method), a phenol-modified dicyclopentadiene resin, and a phenolic resin having a polynaphthylene ether structure (those obtained by subjecting a polyvalent hydroxynaphthalene compound having two or more phenolic hydroxy groups in one molecule to dehydration condensation in the presence of a basic catalyst, using a publicly known method) by a method similar to the above, and a prepolymer thereof. These cyanate compounds may be used singly, or two or more thereof may be appropriately mixed and used.

The method for producing these cyanate compounds is not particularly limited, and a publicly known method can be used. Specific examples thereof include acquisition or synthesis of a hydroxy group containing compound having a desired backbone and cyanation of that compound by modifying the hydroxy group by a publicly known method. Examples of the approach for the cyanation of hydroxy groups include, for example, the approach described in Ian Hamerton, "Chemistry and Technology of Cyanate Ester Resins," Blackie Academic & Professional.

The cured product using these cyanate compounds has a property of being excellent in glass transition temperature, a low thermal expansion property, plating adhesiveness, and the like.

If the bismaleimide compound (B) and the maleimide compound (C) are contained in the resin composition, the content of the cyanate compound is 0.01 to 40 parts by mass based on 100 parts by mass of the total of the bismaleimide compound (B) and the maleimide compound (C).

<Phenolic Resin>

As the phenolic resin, those publicly known in general can be used as long as they are phenolic resins having two or more hydroxyl groups in one molecule. Examples thereof include a bisphenol A-based phenolic resin, a bisphenol E-based phenolic resin, a bisphenol F-based phenolic resin, a bisphenol S-based phenolic resin, a phenol novolac resin, a bisphenol A novolac-based phenolic resin, a glycidyl ester-based phenolic resin, an aralkyl novolac-based phenolic resin, a biphenyl aralkyl-based phenolic resin, a cresol novolac-based phenolic resin, a polyfunctional phenolic resin, a naphthol resin, a naphthol novolac resin, a polyfunctional naphthol resin, an anthracene-based phenolic resin, a naphthalene backbone modified novolac-based phenolic resin, a phenol aralkyl-based phenolic resin, a naphthol aralkyl-based phenolic resin, a dicyclopentadiene-based phenolic resin, a biphenyl-based phenolic resin, an alicyclic phenolic resin, a polyol-based phenolic resin, a phosphorus containing phenolic resin, a polymerizable unsaturated hydrocarbon group containing phenolic resin, and a hydroxyl group containing silicone resin. These phenolic resins may be used singly, or two or more thereof may be appropriately mixed and used.

If the bismaleimide compound (B) and the maleimide compound (C) are contained in the resin composition, the content of the phenolic resin is 0.01 to 40 parts by mass based on 100 parts by mass of the total of the bismaleimide compound (B) and the maleimide compound (C).

<Oxetane Resin>

As the oxetane resin, those publicly known in general can be used. Examples thereof include oxetane, an alkyloxetane such as 2-methyloxetane, 2,2-dimethyloxetane, 3-methyloxetane, and 3,3-dimethyloxetane, 3-methyl-3-methoxymethyloxetane, 3,3-di(trifluoromethyl)perfluorooxetane, 2-chloromethyloxetane, 3,3-bis(chloromethyl)oxetane, biphenyl-based oxetane, OXT-101 (manufactured by Toagosei Co., Ltd., product name), OXT-121 (manufactured by Toagosei Co., Ltd., product name), and OXT-221 (manufactured by Toagosei Co., Ltd., product name). These oxetane resins may be used singly, or two or more thereof may be appropriately mixed and used.

If the bismaleimide compound (B) and the maleimide compound (C) are contained in the resin composition, the content of the oxetane resin is 0.01 to 40 parts by mass based on 100 parts by mass of the total of the bismaleimide compound (B) and the maleimide compound (C).

<Benzoxazine Compound>

As the benzoxazine compound, those publicly known in general can be used as long as they are compounds having two or more dihydrobenzoxazine rings in one molecule. Examples thereof include a bisphenol A-based benzoxazine BA-BXZ (manufactured by Konishi Chemical Ind. Co., Ltd., product name), a bisphenol F-based benzoxazine BF-BXZ (manufactured by Konishi Chemical Ind. Co., Ltd., product name), a bisphenol S-based benzoxazine BS-BXZ (manufactured by Konishi Chemical Ind. Co., Ltd., product name), and a phenolphthalein-based benzoxazine. These benzoxazine compounds may be used singly, or two or more thereof may be appropriately mixed and used.

If the bismaleimide compound (B) and the maleimide compound (C) are contained in the resin composition, the content of the benzoxazine compound is 0.01 to 40 parts by mass based on 100 parts by mass of the total of the bismaleimide compound (B) and the maleimide compound (C).

<Epoxy Resin>

There is no particular limitation on the epoxy resin, and those publicly known in general can be used. Examples thereof include a bisphenol A-based epoxy resin, a bisphenol E-based epoxy resin, a bisphenol F-based epoxy resin, a bisphenol S-based epoxy resin, a bisphenol A novolac-based epoxy resin, a biphenyl-based epoxy resin, a phenol novolac-based epoxy resin, a cresol novolac-based epoxy resin, a xylene novolac-based epoxy resin, a polyfunctional phenol-based epoxy resin, a naphthalene-based epoxy resin, a naphthalene backbone modified novolac-based epoxy resin, a naphthylene ether-based epoxy resin, a phenol aralkyl-based epoxy resin, an anthracene-based epoxy resin, a trifunctional phenol-based epoxy resin, a tetrafunctional phenol-based epoxy resin, triglycidyl isocyanurate, a glycidyl ester-based epoxy resin, an alicyclic epoxy resin, a dicyclopentadiene novolac-based epoxy resin, a biphenyl novolac-based epoxy resin, a phenol aralkyl novolac-based epoxy resin, a naphthol aralkyl novolac-based epoxy resin, an aralkyl novolac-based epoxy resin, a naphthol aralkyl-based epoxy resin, a dicyclopentadiene-based epoxy resin, a polyol-based epoxy resin, a phosphorus containing epoxy resin, a glycidyl amine, a compound obtained by epoxidizing a double bond of butadiene and the like, a compound obtained by the reaction between a hydroxyl group containing silicone resin and epichlorohydrin, and a halide thereof. These epoxy resins may be used singly, or two or more thereof may be appropriately mixed and used.

As the epoxy resin, commercial products can be used, and examples thereof include an epoxy resin represented by the formula (31) (NC-3000FH (product name) manufactured by Nippon Kayaku Co., Ltd., $n_5$ is about 4 in the formula (31)) and a naphthalene-based epoxy resin represented by the formula (32) (HP-4710 (product name) manufactured by DIC CORPORATION).

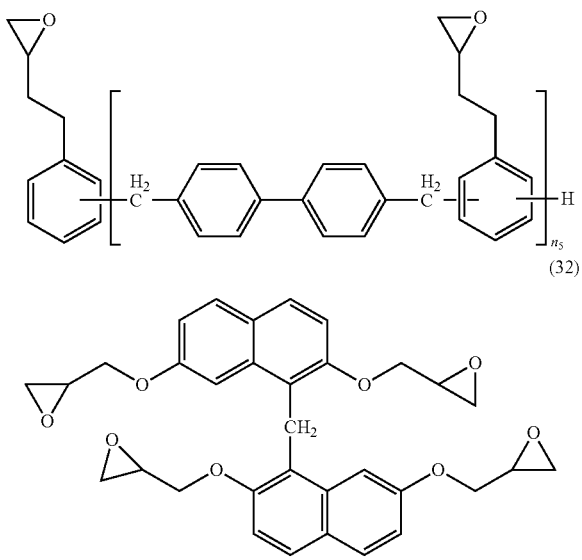

(31)

(32)

These epoxy resins may be used singly, or two or more thereof may be appropriately mixed and used.

If the bismaleimide compound (B) and the maleimide compound (C) are contained in the resin composition, the content of the epoxy resin is 0.01 to 40 parts by mass based on 100 parts by mass of the total of the bismaleimide compound (B) and the maleimide compound (C).

<Additional Compound>

Examples of the additional compound include a vinyl ether such as ethyl vinyl ether, propyl vinyl ether, hydroxyethyl vinyl ether, and ethylene glycol divinyl ether; a styrene such as styrene, methylstyrene, ethylstyrene, and divinylbenzene; triallyl isocyanurate, trimethallyl isocyanurate, and bisallylnadic imide. These compounds may be used singly, or two or more thereof may be appropriately mixed and used.

If the bismaleimide compound (B) and the maleimide compound (C) are contained in the resin composition, the content of the additional compound is 0.01 to 40 parts by mass based on 100 parts by mass of the total of the bismaleimide compound (B) and the maleimide compound (C).

[Organic Solvent]

The resin composition of the present embodiment may contain an organic solvent if required. When an organic solvent is used, the viscosity can be adjusted during the preparation of the resin composition. The type of the organic solvent is not particularly limited as long as it is capable of dissolving a part of or all of the resin in the resin composition. Examples of the organic solvent include halogenated solvents such as dichloromethane, chloroform, dichloroethane, and chlorobenzene; aprotic polar solvents such as dimethylformamide, dimethylacetamide, dimethyl sulfoxide, tetrahydrofuran, dioxane, and acetonitrile; ketone solvents such as acetone, methyl ethyl ketone, methyl isobutyl ketone, cyclopentanone, and cyclohexanone; cellosolve solvents such as 2-ethoxyethanol and propylene glycol monomethyl ether; aliphatic alcohol solvents such as methanol, ethanol, propanol, isopropanol, and butanol; aromatic group-containing phenol solvents such as phenol and cresol; ester solvents such as ethyl lactate, methyl acetate, ethyl acetate, butyl acetate, isoamyl acetate, methyl methoxypropionate, methyl hydroxyisobutyrate, γ-butyrolactone, and propylene glycol monomethyl ether acetate; and aromatic hydrocarbon solvents such as toluene and xylene.

Among these, methyl ethyl ketone, propylene glycol monomethyl ether acetate, and dimethylacetamide are preferable from the viewpoint of exhibiting excellent solubility with the compound (A) and, furthermore, with the additional resin and compound. These organic solvents may be used singly, or two or more thereof may be appropriately mixed and used.

[Additional Component]

In the resin composition of the present embodiment, a variety of polymer compounds such as thermosetting resins, thermoplastic resins and oligomers thereof, and elastomers, which have not been mentioned before; flame retardant compounds, which have not been mentioned before; additive agents and the like can also be used in combination to the extent that the characteristics of the present embodiment are not impaired. These are not particularly limited as long as they are those generally used. Examples of the flame retardant compound include, for example, a nitrogen containing compound such as melamine and benzoguanamine, an oxazine ring containing compound; and a phosphorus compound such as a phosphate compound, an aromatic fused phosphate ester, and a halogen-containing fused phosphate ester. Examples of the additive agent include, for example, an ultraviolet absorbing agent, an antioxidant, a fluorescent brightening agent, a photosensitizer, a dye, a pigment, a thickening agent, a lubricant, a defoaming agent, a surface conditioner, a brightening agent, a polymerization inhibitor and a thermal curing accelerator. These components may be used singly, or two or more thereof may be appropriately mixed and used.

In the resin composition, the content of the additional components is normally each 0.1 to 10 parts by mass based on 100 parts by mass of the resin solid content in the resin composition.

[Resin Composition and Method for Producing Varnish]

The resin composition of the present embodiment can be prepared by appropriately mixing the compound (A), and if required, the bismaleimide compound (B), the maleimide compound (C), the photo initiator (D), the maleimide compound (E), the filler (F), the additional resin, the additional compound, the additive agent, and the like. Examples of the method for producing the resin composition include a method in which each of the components described above is sequentially compounded in a solvent and stirred sufficiently.

Upon producing the resin composition, publicly known treatment (stirring, mixing, and kneading treatment and the like) for uniformly dissolving or dispersing each component can be carried out, if required. Specifically, by using a stirring tank equipped with a stirrer having an appropriate stirring capacity to carry out the stirring and dispersion treatment, the dispersibility of each component such as the compound (A) in the resin composition can be improved. The stirring, mixing, and kneading treatment can be appropriately carried out by using a publicly known apparatus such as a stirring apparatus intended for dispersion such as an ultrasonic homogenizer; an apparatus intended for mixing such as a three roll mill, a ball mill, a bead mill, or a sand mill; or a revolution or rotation mixing apparatus. In addition, upon preparing the resin composition, an organic solvent can be used if required. The type of the organic solvent is not particularly limited as long as it is capable of dissolving the resin in the resin composition, and specific examples thereof are as described above.

The resin composition can be suitably used as a varnish upon fabricating a resin sheet of the present embodiment, which will be mentioned later. The varnish can be obtained by a publicly known method. For example, the varnish can be obtained by adding 10 to 900 parts by mass, preferably 30 to 500 parts by mass of an organic solvent to 100 parts by mass of components other than the organic solvent in the resin composition and carrying out the publicly known treatment (stirring, mixing, kneading treatment or the like). The organic solvent used for preparation of varnish is not particularly limited, and specific examples thereof are as described above.

[Application]

The resin composition of the present embodiment can be suitably used in the production of a multilayer printed wiring board, and can be used preferably in applications where an insulation resin composition is required. For example, the resin composition of the present embodiment can be used for a photosensitive film, a photosensitive film with a support, a prepreg, a resin sheet, a circuit substrate (applications for a laminate, applications for a multilayer printed wiring board, and the like), a solder resist, an underfill material, a die bonding material, a semiconductor sealing material, a hole filling resin, a component embedding resin, and the like. Among the above, the resin composition can be suitably used for an insulation layer of a multilayer printed wiring board or for a solder resist because it is excellent in photocurability, and alkaline developability.

[Cured Product]

The cured product is obtained by curing the resin composition. The cured product can be obtained by, for example, melting the resin composition or dissolving the resin composition in a solvent, then pouring the resin composition into a mold, and curing the resin composition with light under normal conditions. It is preferable to cure the resin composition in a light wavelength range of 100 to 500 nm where curing is efficiently promoted by a photo initiator or the like.

[Resin Sheet]

A resin sheet of the present embodiment is a resin sheet with a support containing: a support; and a resin layer disposed on one surface or both surfaces of the support, wherein the resin layer contains the resin composition of the present embodiment. The resin sheet can be produced by applying the resin composition onto the support and drying it. The resin layer in the resin sheet has excellent photocurability and alkaline developability.

As the support, those publicly known can be used and there is no particular limitation thereon, but it is preferably a resin film. Examples of the resin film include a polyimide film, a polyamide film, a polyester film, a polyethylene terephthalate (PET) film, a polybutylene terephthalate (PBT) film, a polypropylene (PP) film, a polyethylene (PE) film, a polyethylene naphthalate film, a polyvinyl alcohol film, and a triacetyl acetate film. Among the above, a PET film is preferable.

Preferably, the surface of the resin film is coated with a release agent in order to facilitate release from the resin layer. The thickness of the resin film is preferably in the range of 5 to 100 μm and more preferably in the range of 10 to 50 μm. When the thickness is less than 5 μm, the support tends to be easily torn at the time when the support is released before alkaline development, and when the thickness is greater than 100 μm, the resolution upon being exposed through the support tends to be reduced.

In addition, in order to reduce light scattering during exposure, it is preferable that the resin film should have excellent transparency.

Furthermore, in the resin sheet, the resin layer thereof may be protected with a protective film.

By protecting the resin layer side with a protective film, adhesion of dust and the like to the surface of the resin layer and scratches can be prevented. As the protective film, a film composed of a material similar to the resin film can be used. The thickness of the protective film is preferably in the range of 1 to 50 μm and more preferably in the range of 5 to 40 μm. If the thickness is less than 1 μm, the handleability of the protective film tends to be reduced, and if the thickness is greater than 50 μm, the inexpensiveness tends to be poor. Note that it is preferable for the protective film to have a smaller adhesive force between the resin layer and the protective film than the adhesive force between the resin layer and the support.

Examples of the method for producing the resin sheet include a method in which the resin composition is applied to a support such as PET film and the organic solvent is removed by drying to produce the resin sheet.

The application method can be carried out by a publicly known method using, for example, a roll coater, a comma coater, a gravure coater, a die coater, a bar coater, a lip coater, a knife coater, a squeeze coater, or the like. The drying can be carried out by, for example, a method of heating in a dryer at 60 to 200° C. for 1 to 60 minutes.

The amount of organic solvent remaining in the resin layer is preferably less than 5% by mass based on the total mass of the resin layer from the viewpoint of preventing diffusion of the organic solvent in the subsequent steps. It is preferable that the thickness of the resin layer should be 1 to 50 μm from the viewpoint of improving handleability.

The resin sheet can be preferably used for production of insulation layers of multilayer printed wiring boards.

[Multilayer Printed Wiring Board]

The multilayer printed wiring board in the present embodiment contains an insulation layer; and a conductor layer formed on one surface or both surfaces of the insulation layer, wherein the insulation layer contains the resin composition of the present embodiment. The insulation layer can also be obtained by, for example, laminating one or more of the resin sheets and curing them. The number of laminations in the insulation layer and the conductor layer can be appropriately set according to an intended application. The order of the insulation layer and the conductor layer is not particularly limited. The conductor layer may be a metal foil used for various printed wiring board materials, and examples thereof include metal foils of copper, aluminum and the like. Examples of the copper metal foil include a rolled copper foil and an electrolytic copper foil. The thickness of the conductor layer is normally 1 to 100 μm. In particular, it can be produced by the following method.

(Lamination Step)

In a lamination step, the resin layer side of the resin sheet is laminated to one surface or both surfaces of a circuit substrate using a vacuum laminator. Examples of the circuit substrate include, for example, a glass epoxy substrate, a metal substrate, a ceramic substrate, a silicon substrate, a semiconductor sealing resin substrate, a polyester substrate, a polyimide substrate, a BT resin substrate, and a thermosetting polyphenylene ether substrate. Note that a circuit substrate refers to a substrate in which a patterned conductor layer (circuit) is formed on one surface or both surfaces of a substrate as described above. Also, in a multilayer printed wiring board formed by alternately laminating a conductor layer and an insulation layer, a substrate in which one surface or both surfaces of the outermost layer of the multilayer printed wiring board are patterned conductor layers (circuits) is also included in the circuit substrate. Note that the insulation layer laminated on the multilayer printed wiring board may be an insulation layer obtained by laminating and curing one or more resin sheets of the present embodiment, or an insulation layer obtained by laminating one or more resin sheets of the present embodiment and one or more publicly known resin sheets different from the resin sheet of the present embodiment. Note that the mode in which the resin sheets of the present embodiment and the publicly known resin sheets different from the resin sheet of the present embodiment are laminated is not particularly limited. The surface of the conductor layer may be subjected to blackening treatment and/or roughening treatment by copper etching or the like in advance. In the lamination step, when the resin sheet has a protective film, the protective film is peeled off and removed. Then, the resin sheet and the circuit substrate are preheated if required, and while pressurizing and heating the resin layer of the resin sheet, it is crimped to the circuit substrate. In the present embodiment, a method of laminating the resin layer of the resin sheet to the circuit substrate under reduced pressure using a vacuum lamination method is suitably used.

As conditions of the lamination step, for example, it is preferable to perform the lamination under reduced pressure with a crimping temperature (lamination temperature) of 50 to 140° C., crimping pressure of 1 to 15 kgf/cm$^2$, crimping time of 5 to 300 seconds, and air pressure of 20 mmHg or less. Also, the lamination step may be in a batch type or in a continuous type using a roll. The vacuum lamination method can be carried out using a commercially available vacuum laminator. Examples of the commercially available vacuum laminator include, for example, a two-stage build-up laminator manufactured by Nikko-Materials Co., Ltd.

(Exposure Step)

In the exposure step, after providing the resin layer on the circuit substrate by the lamination step, a predetermined portion of the resin layer is irradiated with an active energy ray as a light source to cure the resin layer in the irradiated part. The compound (A) does not inhibit the photocuring reaction in the exposure step.

The irradiation may be performed through a mask pattern or may be performed by using the direct imaging method in which the irradiation is directly applied. Examples of the active energy ray include, for example, ultraviolet rays, visible rays of light, electron beam, and X-rays. The wavelength of the active energy ray is, for example, in the range of 200 to 600 nm. When an ultraviolet ray is used, the irradiation amount thereof is approximately 10 to 1000 mJ/cm$^2$. Upon producing a printed wiring board having a highly dense and highly detailed wiring formation (pattern) using the stepper exposure method, it is preferable to use, for example, an active energy ray including a wavelength of 365 nm (i-line) as an active energy ray. When an active energy ray including a wavelength of 365 nm (i-line) is used, the irradiation amount is approximately 10 to 10,000 mJ/cm$^2$. Upon producing a printed wiring board having a highly dense and highly detailed wiring formation (pattern) using the direct imaging method, it is preferable to use, for example, an active energy ray including a wavelength of 405 nm (h-line) as an active energy ray. When an active energy ray including a wavelength of 405 nm (h-line) is used, the irradiation amount is approximately 10 to 10,000 mJ/cm$^2$.

There are two exposure methods for passing through the mask pattern: the contact exposure method, in which the mask pattern is adhered to the multilayer printed wiring board, and the non-contact exposure method, in which parallel light rays are used to perform the exposure without adhering the mask pattern to the multilayer printed wiring board, but either method may be used. Also, when a support is present on the resin layer, it may be exposed from the top of the support, or it may be exposed after the support is removed.

(Alkaline Development Step)

When a support is not present on the resin layer, a portion which is not photocured directly in alkaline development (unexposed portion) is removed after the exposure step, and development is performed, whereby an insulation layer pattern can be formed.

When a support is present on the resin layer, the support is removed after the exposure step, and thereafter a portion which is not photocured in alkaline development (unexposed portion) is removed, and development is performed, whereby an insulation layer pattern can be formed.

Since the unexposed resin layer containing the resin composition of the present embodiment contains the compound (A), it has excellent alkaline developability and the unexposed resin composition can be quickly removed. Therefore, it is possible to obtain a printed wiring board having a highly detailed pattern.

In the case of alkaline development, the developing solution is not particularly limited as long as unexposed portion is selectively eluted, and alkaline developing solutions such as an aqueous tetramethylammonium hydroxide solution, an aqueous sodium carbonate solution, an aqueous potassium carbonate solution, an aqueous sodium hydroxide solution and an aqueous potassium hydroxide solution are used. In the present embodiment, it is more preferable to use an aqueous tetramethylammonium hydroxide solution. These alkaline developing solutions may be used singly, or two or more thereof may be appropriately mixed and used.

As the alkaline development method, for example, a known method such as dipping, paddling, spraying, shaking immersion, blushing and scraping can be carried out. In pattern formation, these development methods can be used in combination if necessary. As the development method, use of a high-pressure spray is suitable because the resolution is further improved. When the spraying method is employed, the spray pressure is preferably 0.02 to 0.5 MPa.

(Postbaking Step)

In the present embodiment, a postbaking step is carried out after the alkaline development step, thereby forming an insulation layer (cured product). Examples of the postbaking step include an ultraviolet irradiation step with a high pressure mercury lamp and a heating step using a clean oven, and these steps may be used in combination as well. When irradiating with ultraviolet ray, the irradiation amount thereof can be adjusted if required, and for example, the irradiation can be carried out at an irradiation amount of approximately 0.05 to 10 J/cm$^2$. Also, the conditions of heating can be appropriately selected if required, but they are preferably selected from the range of 20 to 180 minutes at 150 to 220° C., and more preferably from the range of 30 to 150 minutes at 160 to 200° C.

(Conductor Layer Formation Step)

After forming the insulation layer (cured product), a conductor layer is formed on the surface of the insulation layer by dry plating.

Note that upon forming the conductor layer, a surface modification treatment may be performed on the surface of the insulation layer before dry plating. For the surface modification treatment, a publicly known method such as plasma etching, reverse sputtering, and corona treatment can be used.

For the dry plating, a publicly known method such as a vapor deposition method, a sputtering method, and an ion plating method can be used. In the vapor deposition method (vacuum deposition method), for example, a metallic film can be formed on the insulation layer by placing the multilayer printed wiring board in a vacuum container and heating and evaporating the metal. In the sputtering method as well, for example, the multilayer printed wiring board is placed in a vacuum container, an inert gas such as argon is introduced, a direct current voltage is applied, the ionized inert gas is brought into collision with the target metal, and the knocked-out metal can be used to form a metallic film on the insulation layer.

Next, a conductor layer is formed by nonelectrolytic plating or electroplating. As a method of subsequent pattern formation, for example, a subtractive method, a semi-additive method, or the like can be used.

[Semiconductor Device]

A semiconductor device of the present embodiment contains the resin composition of the present embodiment. In particular, it can be produced by the following method. A semiconductor device can be produced by a mounting semiconductor chip at the conduction points on the multilayer printed wiring board. Here, the conduction points refer to the points in the multilayer printed wiring board where electrical signals are conveyed, and the locations thereof may be on the surface or at embedded points. In addition, the semiconductor chip is not particularly limited as long as they are electrical circuit elements made of semiconductors.

The method for mounting the semiconductor chip upon producing the semiconductor device is not particularly limited as long as the semiconductor chip effectively functions. Specific examples thereof include a wire bonding mounting method, a flip chip mounting method, a mounting method with a bumpless build-up layer (BBUL), a mounting method with an anisotropic conductive film (ACF), and a mounting method with a non-conductive film (NCF).

Alternatively, the semiconductor device can be produced by forming an insulation layer containing the resin composition on a semiconductor chip or a substrate on which semiconductor chip is mounted. The shape of the substrate on which semiconductor chip is mounted may be wafer-like or panel-like. After the formation, the semiconductor device can be produced using the same method as the multilayer printed wiring board described above.

EXAMPLES

The present embodiment will be more specifically described below using Examples and Comparative Examples. The present embodiment is not limited in any way by the following Examples.

[Synthesis of Maleimide Compound (TMDM)]

Synthetic Example 1

The compound (TMDM) represented by formula (21) was synthesized as follows.

[Synthesis of Amide Acid Compound (Hereinafter Referred to as MA-TMDA)]

First, MA-TMDA represented by formula (33) was synthesized by the following method.

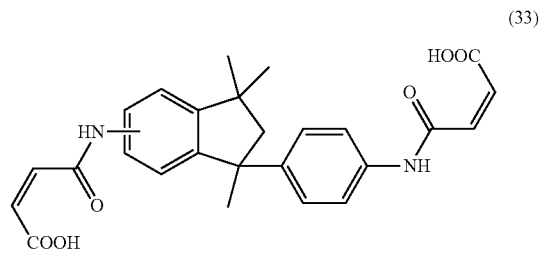

(33)

To a 100-mL four necked flask equipped with an argon inlet, a Dean-Stark apparatus, a Dimroth condenser tube, and a thermometer, 5.2 g (53 mmol) of maleic anhydride, 20 mL of N-methylpyrrolidone (NMP), and 20 mL of toluene were added, and the mixture was stirred at room temperature (25° C.) under an argon stream to completely dissolve the maleic anhydride. To this solution was added 5.0 g (19 mmol) of TMDA (manufactured by Nipponjunryo Chemicals Co., Ltd., a mixture of 5-amino-1,3,3-trimethyl-1-(4-aminophenyl)-indane and 6-amino-1,3,3-trimethyl-1-(4-aminophenyl)-indane) and 10 mL of NMP, and the mixture was stirred at room temperature (25° C.) for 17 hours.

The reaction solution was partially collected, to which water and ethyl acetate were added, and then the mixture was shaken. Then, the organic layer was removed and dried over magnesium sulfate. The solvent in the supernatant was distilled off at 40° C. to obtain a yellow oil. $^1$H-NMR measurement was carried out to confirm that it was MA-TMDA represented by formula (33).

The $^1$H-NMR assignments for MA-TMDA represented by formula (33) are shown below. The $^1$H-NMR chart is also shown in FIG. 1.

$^1$H-NMR (300 MHz, DMSO-d6) δ (ppm): 10.40 (m, 2H, —COOH), 7.30 (m, 7H, ArH), 6.33 (m, 4H, =CH—), 2.11 (m, 2H, —CH$_2$—), 1.48 (d, 3H, —CH$_3$), 1.21 (d, 3H, —CH$_3$), 0.92 (d, 3H, —CH$_3$)

[Synthesis of TMDM]

To the above reaction solution, 0.67 g (3.5 mmol) of p-toluenesulfonic acid monohydrate was added, and the mixture was heated under reflux at 127° C. for 2.5 hours. After cooling to room temperature (25° C.), the cooled reaction solution was poured into a mixed solution of 50 mL of saturated aqueous solution of sodium bicarbonate and 100 mL of ethyl acetate while stirring. Furthermore, 100 mL of water and 100 mL of ethyl acetate were added, and the mixture was stirred and allowed to stand for 5 minutes. Then, the mixture was separated and the aqueous layer was extracted three times with 50 mL of ethyl acetate. All the organic layers were combined and washed once with 100 mL of water, once with 10 mL of saturated brine, and twice with 5 mL of saturated brine. After drying over magnesium sulfate and filtering off the solid, the solvent was distilled off at 40° C. to obtain a yellow solid.

The obtained yellow solid was dissolved in 6.5 mL of acetone, and the acetone solution was poured into 300 mL of water. The precipitated solid was filtered and washed with a small amount of isopropyl alcohol (IPA), and then dried at 50° C. for 20 hours under reduced pressure to obtain 5.71 parts by mass of a yellow solid. $^1$H-NMR measurement was carried out to confirm that it was the maleimide compound (TMDM) represented by formula (21).

Figure 2:
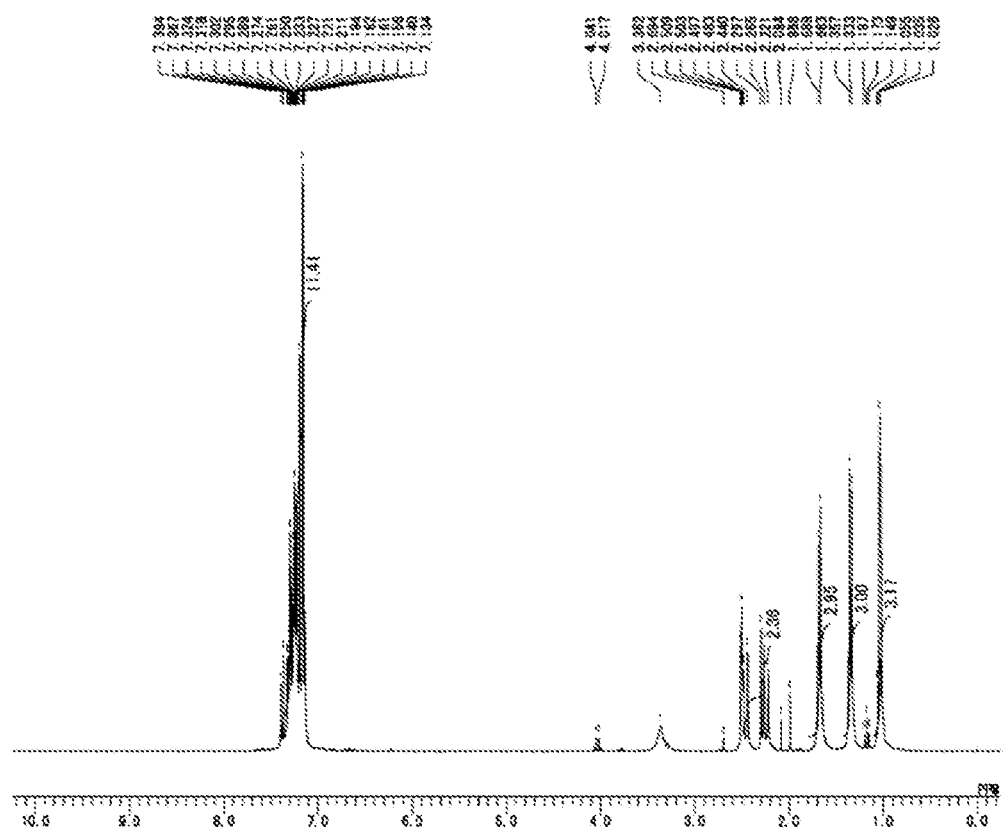
FIG. 2 shows the $^1$H-NMR chart of a maleimide compound (TMDM).

The $^1$H-NMR assignments for TMDM are shown below. The $^1$H-NMR chart is also shown in FIG. 2.

¹H-NMR (300 MHz, DMSO-d6) δ (ppm): 7.19 (m, 11H, ArH, —CH═CH—), 2.42 (m, 2H, —CH$_2$—), 1.66 (d, 3H, —CH$_3$), 1.32 (d, 3H, —CH$_3$), 1.00 (d, 3H, —CH$_3$)

[Synthesis of Compound Represented by Formula (16)]

Example 1

The compound represented by formula (16) (also referred to as component (A-1)) was synthesized as follows.

To a 200-mL flask were added 6.56 g (55.5 mmol) of 1,10-decanediol (manufactured by Tokyo Kasei Kogyo Co., Ltd.), 23.10 g (116.6 mmol) of cyclohexane-1,2,4-tricarboxylic acid-1,2-anhydride (manufactured by Mitsubishi Gas Chemical Company, Inc., H-TMAn (product name)), 6.77 g (55.5 mmol) of 4-dimethylaminopyridine, 12.35 g of triethylamine, and 60 g of dichloromethane, and the mixture was stirred at room temperature (25° C.) for 7 hours.

To the reaction solution were added 100 mL of water and 50 mL of dichloromethane, and the mixture was stirred for another hour. In addition, 150 mL of dichloromethane and 50 mL of 1M hydrochloric acid were added, and the mixture was separated to remove the aqueous layer. To the obtained organic layer, 60 mL of 1M hydrochloric acid was added and the mixture was stirred. After separating the mixture and removing the aqueous layer, the mixture was washed twice with 60 mL of 1M hydrochloric acid, once with 60 mL of water, and once with 30 mL of saturated brine, then dried over magnesium sulfate, and the solvent was distilled off. 10.96 g of a white solid was obtained by vacuum drying at 80° C. ¹H-NMR measurement was carried out to confirm that it was the compound (A-1) represented by formula (16).

Figure 3:
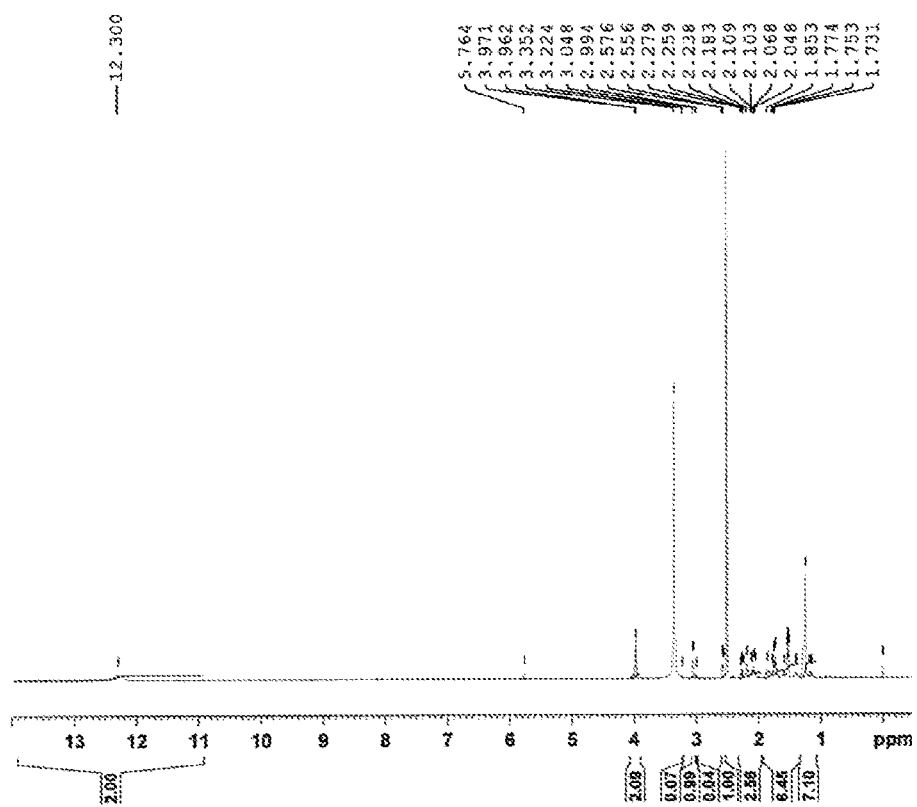
FIG. 3 shows the $^1$H-NMR chart of the compound (A-1).

The ¹H-NMR assignments for the compound (A-1) are shown below. The ¹H-NMR chart is also shown in FIG. 3.

¹H-NMR (500 MHz, DMSO-d6) δ (ppm): 12.30 (s, 4H, —COOH), 3.97 (m, 4H), 3.05 (s, 2H), 2.57 (m, 2H), 2.3-1.1 (m, 32H)

[Synthesis of Compound Represented by Formula (17)]

Example 2

The compound represented by formula (17) (also referred to as component (A-2)) was synthesized as follows.

To a 200-mL flask were added 8.71 g (50 mmol) of 1,10-decanediol (manufactured by Tokyo Kasei Kogyo Co., Ltd.), 20.81 g (105 mmol) of cis,cis-cyclohexane-1,2,4-tricarboxylic acid-1,2-anhydride (manufactured by Mitsubishi Gas Chemical Company, Inc., H-TMAn-S (product name)), 6.10 g (50 mmol) of 4-dimethylaminopyridine, 11.13 g of triethylamine, and 60 g of dichloromethane, and the mixture was stirred at room temperature (25° C.) for 3 hours.

To the reaction solution were added 50 mL of water and 6 mL of methanol, and the mixture was stirred for another hour. 100 mL of 1M hydrochloric acid was added and the mixture was stirred. After removing the aqueous layer, another 100 mL of 1M hydrochloric acid was added and the mixture was stirred. Again, the aqueous layer was removed, and 100 mL of 1M hydrochloric acid was added. The precipitated white solid was collected by suction filtration and washed three times with 200 mL of water. 18.84 g of a white solid was obtained by vacuum drying at 40° C. ¹H-NMR measurement was carried out to confirm that it was the compound (A-2) represented by formula (17).

Figure 4:
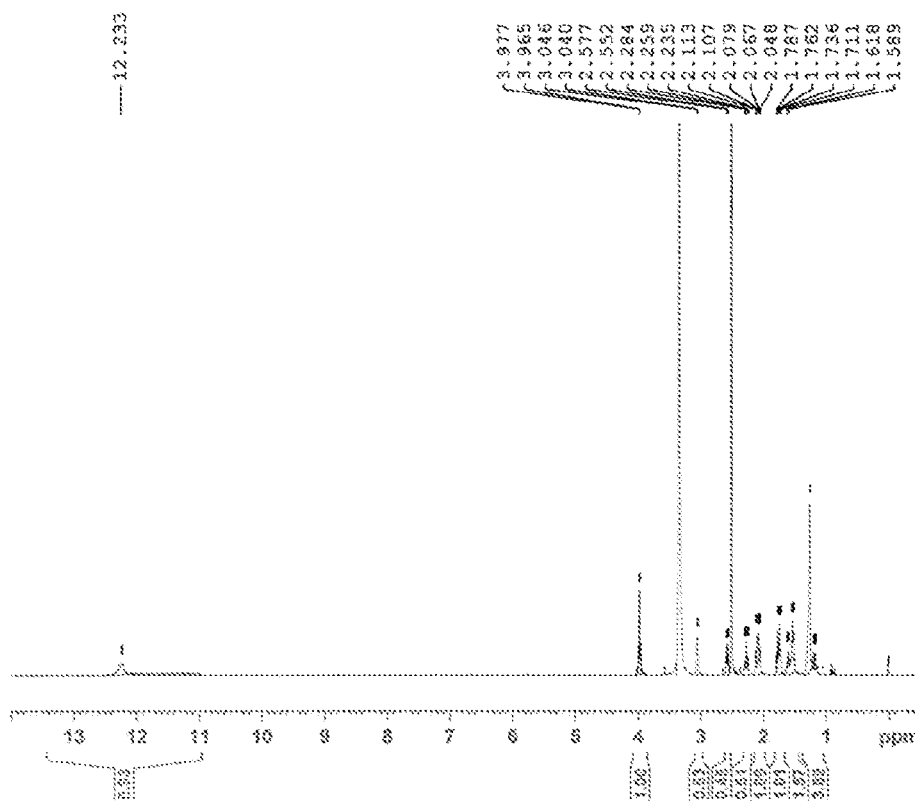
FIG. 4 shows the $^1$H-NMR chart of the compound (A-2).

The ¹H-NMR assignments for the compound (A-2) are shown below. The ¹H-NMR chart is also shown in FIG. 4.

¹H-NMR (500 MHz, DMSO-d6) δ (ppm): 12.23 (s, 4H, —COOH), 3.97 (m, 4H), 3.05 (m, 2H), 2.57 (m, 2H), 2.3-1.1 (m, 32H)

[Synthesis of Compound Represented by Formula (18)]

Example 3

The compound represented by formula (18) (also referred to as component (A-3)) was synthesized as follows.

To a 200-mL flask were added 5.91 g (50 mmol) of 1,6-hexanediol (manufactured by Tokyo Kasei Kogyo Co., Ltd.), 20.81 g (105 mmol) of cis,cis-cyclohexane-1,2,4-tricarboxylic acid-1,2-anhydride (manufactured by Mitsubishi Gas Chemical Company, Inc., H-TMAn-S (product name)), 6.10 g (50 mmol) of 4-dimethylaminopyridine, 11.13 g of triethylamine, and 60 g of dichloromethane, and the mixture was stirred at room temperature (25° C.) for 8 hours.

To the reaction solution was added 50 mL of water, and the mixture was stirred for another hour, then 50 mL of 1M hydrochloric acid was added. 100 mL of methyl isobutyl ketone and 100 mL of 1M hydrochloric acid were added, and the mixture was separated to remove the aqueous layer. To the obtained aqueous layer was added 200 mL of 1M hydrochloric acid, and the precipitated white solid was collected by suction filtration. The collected solid was washed twice with 70 mL of 1M hydrochloric acid and twice with 100 mL of water, and dried in vacuum at 50° C. to obtain 18.40 g of a white solid. ¹H-NMR measurement was carried out to confirm that it was the compound (A-3) represented by formula (18).

Figure 5:
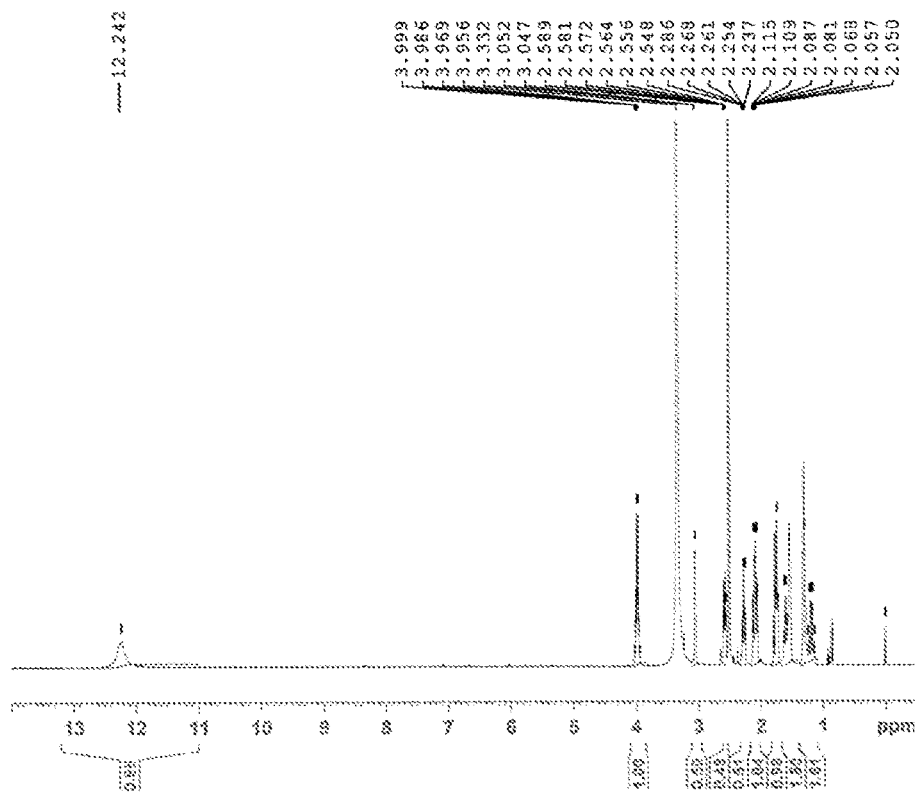
FIG. 5 shows the $^1$H-NMR chart of the compound (A-3).

The ¹H-NMR assignments for the compound (A-3) are shown below. The ¹H-NMR chart is also shown in FIG. 5.

¹H-NMR (500 MHz, DMSO-d6) δ (ppm): 12.24 (s, 4H, —COOH), 3.98 (m, 4H), 3.05 (m, 2H), 2.57 (m, 2H), 2.3-1.1 (m, 22H)

[Evaluation of Raw Material]

[Transmittance and Absorbance]

Using the compound (A-1) as the compound (A), an N-methylpyrrolidone solution containing the compound (A-1) at 1% by mass was prepared, and measurement of the transmittance at each of a wavelength of 365 nm and a wavelength of 405 nm was carried out using a UV-vis measuring apparatus (Hitachi Spectrophotometer U-4100 manufactured by Hitachi High-Technologies Corporation).

Similarly, the compound (A-2) or the compound (A-3) was used as the compound (A) to measure the respective absorbances at wavelengths of 365 nm and 405 nm.

As the bismaleimide compound (B), MIZ-001 (product name, mass average molecular weight (Mw): 3000) manufactured by Nippon Kayaku Co., Ltd. was used to prepare a chloroform solution containing this MIZ-001 (product name) at 1% by mass, and measurement of the transmittance at each of a wavelength of 365 nm and a wavelength of 405 nm was carried out using an UV-vis measuring apparatus (Hitachi Spectrophotometer U-4100 (product name) manufactured by Hitachi High-Technologies Corporation).

As the photo initiator (D), bis(2,4,6-trimethylbenzoyl)-phenylphosphine oxide (Omnirad (registered trademark) 819 (product name) manufactured by IGM Resins B.V.) was used to prepare a chloroform solution containing this Omnirad (registered trademark) 819 (product name) at 0.01% by mass, and measurement of the absorbance at each of a wavelength of 365 nm and a wavelength of 405 nm was carried out using an UV-vis measuring apparatus (U-4100 (product name)).

The results are shown in Table 1.

TABLE 1

| | | Transmittance at 365 nm [%] | Transmittance at 405 nm [%] | Absorbance at 365 nm [—] | Absorbance at 405 nm [—] |
|---|---|---|---|---|---|
| Compound (A) | Compound (A-1) | 98 | 99 | — | — |
| | Compound (A-2) | 98 | 99 | — | — |
| | Compound (A-3) | 99 | 99 | — | — |
| Bismaleimide Compound (B) | MIZ-001 | 19 | 88 | — | — |
| Photo Initiator (D) | Omnirad819 | — | — | 0.32 | 0.18 |

Example 4

[Fabrication of Resin Composition and Resin Sheet]

10 parts by mass of the compound (A-1) as the compound (A), 60 parts by mass of MIZ-001 (product name, mass average molecular weight (Mw): 3000) manufactured by Nippon Kayaku Co., Ltd. as the bismaleimide compound (B), 25 parts by mass of BCPH13 (product name) manufactured by Gunei Chemical Industry Co., Ltd. as the maleimide compound (C), 15 parts by mass of TMDM as the maleimide compound (C), and 5 parts by mass of bis(2,4, 6-trimethylbenzoyl)-phenylphosphine oxide (Omnirad (registered trademark) 819 (product name) manufactured by IGM Resins B.V.) as the photo initiator (D) were mixed, to which 172.5 parts by mass of methyl ethyl ketone (manufactured by Idemitsu Kosan Co., Ltd.) was added, and then the mixture was heated and stirred using a water bath at 70° C., thereby obtaining a varnish (resin composition). This varnish was added dropwise onto a 38-μm-thick PET film (Unipeel (registered trademark) TR1-38 (product name) manufactured by UNITIKA LTD.) and a coating film was formed by spin coating (300 rpm for 10 seconds, followed by 1000 rpm for 30 seconds). The obtained coating film was dried at 90° C. for 5 minutes to obtain a resin sheet with a PET film as the support and a resin layer thickness of 10 μm.

(Fabrication of Resin for Evaluation)

The resin surfaces of the obtained resin sheets were pasted together, and a vacuum laminator (manufactured by Nikko-Materials Co., Ltd.) was used to perform vacuum drawing (5.0 hPa or less) for 30 seconds, followed by lamination molding at a pressure of 10 kgf/cm² and a temperature of 70° C. for 30 seconds. Furthermore, by performing lamination molding at a pressure of 7 kgf/cm² and a temperature of 70° C. for 60 seconds, a resin for evaluation with supports on both surfaces was obtained.

(Fabrication of Inner Layer Circuit Substrate)

After forming an inner layer circuit in a BT (bismaleimide triazine) resin laminate with a glass cloth base material, both surfaces of which are copper clad (copper foil thickness of 18 μm, thickness of 0.2 mm, CCL (registered trademark)-HL832NS (product name) manufactured by Mitsubishi Gas Chemical Company, Inc.), both surfaces were subjected to roughening treatment for copper surfaces with CZ8100 (product name) manufactured by MEC Co., Ltd., thereby obtaining an inner layer circuit substrate.

(Fabrication of Laminate for Evaluation)

The resin surface of the obtained resin sheet was disposed on the copper surface (one surface) of the inner layer circuit substrate described above, and a vacuum laminator (manufactured by Nikko-Materials Co., Ltd.) was used to perform vacuum drawing (5.0 hPa or less) for 30 seconds, followed by lamination molding at a pressure of 10 kgf/cm² and a temperature of 70° C. for 30 seconds. Furthermore, by performing lamination molding at a pressure of 10 kgf/cm² and a temperature of 70° C. for 60 seconds, a laminate for evaluation in which the inner layer circuit substrate, the resin layer and the support were laminated was obtained.

Example 5

A varnish and a resin sheet were obtained in the same manner as in Example 4, except that 7.5 parts by mass of the compound (A-1) was used instead of 10 parts by mass of the compound (A-1) and 168.8 parts by mass of methyl ethyl ketone was used instead of 172.5 parts by mass of methyl ethyl ketone. In addition, using the resin sheet, a resin for evaluation and a laminate for evaluation were obtained in the same manner as in Example 4.

Example 6

A varnish and a resin sheet were obtained in the same manner as in Example 4, except that 7.5 parts by mass of the compound (A-2) was used instead of 10 parts by mass of the compound (A-1) as the compound (A) and 168.8 parts by mass of methyl ethyl ketone was used instead of 172.5 parts by mass of methyl ethyl ketone. In addition, using the resin sheet, a resin for evaluation and a laminate for evaluation were obtained in the same manner as in Example 4.

Example 7

A varnish and a resin sheet were obtained in the same manner as in Example 4, except that 5 parts by mass of the compound (A-2) was used instead of 10 parts by mass of the compound (A-1) as the compound (A) and 165.0 parts by mass of methyl ethyl ketone was used instead of 172.5 parts by mass of methyl ethyl ketone. In addition, using the resin sheet, a resin for evaluation and a laminate for evaluation were obtained in the same manner as in Example 4.

Example 8

A varnish and a resin sheet were obtained in the same manner as in Example 4, except that 7.5 parts by mass of the compound (A-3) was used instead of 10 parts by mass of the compound (A-1) as the compound (A) and 168.8 parts by mass of methyl ethyl ketone was used instead of 172.5 parts by mass of methyl ethyl ketone. In addition, using the resin sheet, a resin for evaluation and a laminate for evaluation were obtained in the same manner as in Example 4.

Example 9

A varnish and a resin sheet were obtained in the same manner as in Example 4, except that 5 parts by mass of the compound (A-3) was used instead of 10 parts by mass of the compound (A-1) as the compound (A) and 165.0 parts by mass of methyl ethyl ketone was used instead of 172.5 parts by mass of methyl ethyl ketone. In addition, using the resin sheet, a resin for evaluation and a laminate for evaluation were obtained in the same manner as in Example 4.

Comparative Example 1

A varnish and a resin sheet were obtained in the same manner as in Example 4, except that 10 parts by mass of 1,10-decanediol (manufactured by Tokyo Kasei Kogyo Co., Ltd.) was used instead of 10 parts by mass of the compound (A-1). In addition, using the resin sheet, a resin for evaluation and a laminate for evaluation were obtained in the same manner as in Example 4.

Comparative Example 2

A varnish and a resin sheet were obtained in the same manner as in Example 4, except that 10 parts by mass of 1,6-hexanediol (manufactured by Tokyo Kasei Kogyo Co., Ltd.) was used instead of 10 parts by mass of the compound (A-1). In addition, using the resin sheet, a resin for evaluation and a laminate for evaluation were obtained in the same manner as in Example 4.

[Evaluation]

Figure 6:
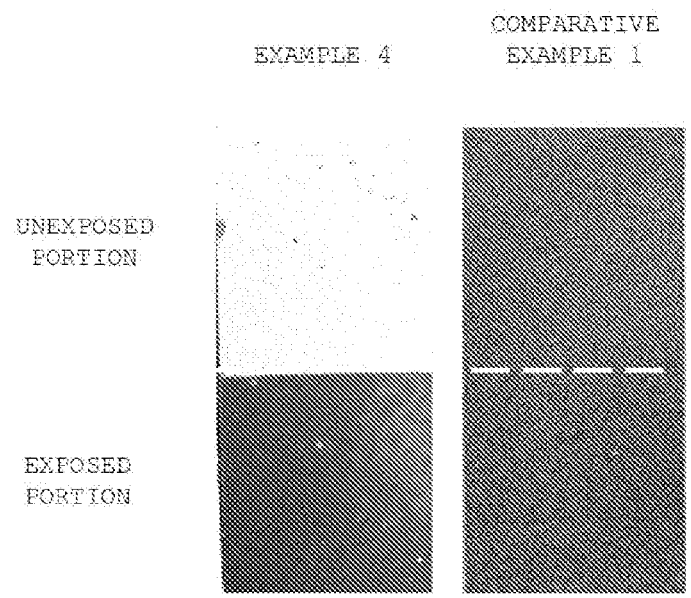
FIG. 6 shows photographs after alkaline development performed with the use of resin sheets obtained using an active energy ray including a wavelength of 405 nm (h-line) in Example 4 and Comparative Example 1.

The resins for evaluation and the laminates for evaluation, which had been obtained in Examples and Comparative Examples, were measured and evaluated in accordance with the following methods. The results are shown in Table 2 and FIG. 6.

<Photocurability>

By using a photo DSC (DSC-2500 (brand name) manufactured by TA Instruments Japan Inc.) equipped with a light source (Omnicure (registered trademark) 52000 (product name) manufactured by U-VIX Corporation) that is capable of being irradiated with an active energy ray including a wavelength of 200 to 600 nm, the obtained resin for evaluation was irradiated with an active energy ray including a wavelength of 200 to 600 nm at an illuminance of 30 mW and for an exposure time of 3.5 minutes, thereby obtaining a graph of time (sec) on the horizontal axis and heat flow (mW) on the vertical axis.

A graph of time (sec) on the horizontal axis and heat flow (mW) on the vertical axis was obtained under the same conditions as described above except that a filter for a ray with a wavelength of 405 nm (h-line) was used, and an active energy ray including a wavelength of 405 nm (h-line) was used as a light source.

In each graph, the enthalpy (J/g) was defined as the peak area when a line was drawn horizontally from the endpoint of the graph. The curability was evaluated in accordance with the following criteria.

"AA": enthalpy was 1 (J/g) or more.
"CC": enthalpy was less than 1 (J/g).

Note that an enthalpy of 1 (J/g) or more meant that the curing of the resin is sufficiently advanced by exposure at a predetermined wavelength.

<Alkaline Developability>

Using a light source capable of applying an active energy ray including a wavelength of 405 nm (h-line) (MA-20 (product name) manufactured by MIKASA CO., LTD), the obtained laminate for evaluation was irradiated from above the support at an irradiation amount of 300 mJ/cm$^2$ to expose a half of the resin layer while the other half is unexposed. Thereafter, the support (PET film) was peeled, and the laminate was shaken in aqueous 2.38% TMAH (tetramethylammonium hydroxide) solution (developing solution, manufactured by Tokuyama Corporation) for 180 seconds. The alkaline developability was visually evaluated in accordance with the following criteria.

"AA": the exposed portion was not dissolved, and the unexposed portion was dissolved by shaking for 180 seconds.

"AB": the exposed portion was not dissolved. The unexposed portion was partially dissolved by shaking for 180 seconds, but remained partially undissolved.

"CC": either the exposed portion or the unexposed portion was not dissolved.

FIG. 5 shows photographs after alkaline development performed with the use of the resin sheets which were obtained in Example 4 and Comparative Example 1.

TABLE 2

| | | Example 4 | Example 5 | Example 6 | Example 7 | Example 8 | Example 9 | Comparative Example 1 | Comparative Example 2 |
|---|---|---|---|---|---|---|---|---|---|
| Compound (A) | Compound (A-1) | 10 | 7.5 | | | | | | |
| | Compound (A-2) | | | 7.5 | 5 | | | | |
| | Compound (A-3) | | | | | 7.5 | 5 | | |
| Compound | 1,10-Decanediol | | | | | | | 10 | |
| | 1,6-Hexanediol | | | | | | | | 10 |
| Bismaleimide Compound (B) | MIZ-001 | 60 | 60 | 60 | 60 | 60 | 60 | 60 | 60 |
| Maleimide | BCPH13 | 25 | 25 | 25 | 25 | 25 | 25 | 25 | 25 |
| Compound (C) | TMDM | 15 | 15 | 15 | 15 | 15 | 15 | 15 | 15 |
| Photo Initiator (D) | Omnirad819 | 5 | 5 | 5 | 5 | 5 | 5 | 5 | 5 |
| Evaluation | Photocurability (405 nm) | AA | AA | AA | AA | AA | AA | AA | AA |
| | Photocurability (200-600 nm) | AA | AA | AA | AA | AA | AA | AA | AA |
| | Alkaline Developability | AA | AB | AA | AA | AA | AA | CC | CC |

Table 2 reveals that according to the present embodiment, exposure with any of an active energy ray including a wavelength of 405 nm (h-line) and an active energy ray including a wavelength of 200 to 600 nm ensures that the resin composition is properly light-sensitive and can be photocured. According to the present embodiment, a cured product having excellent alkaline developability can be obtained.

The present application is based on Japanese Patent Application No. 2019-223952 filed on Dec. 11, 2019, the contents of which are incorporated herein by reference.

INDUSTRIAL APPLICABILITY

The resin composition of the present embodiment can be suitably used in the production of a multilayer printed wiring board, and can be used preferably in applications where an insulation resin composition is required, and therefore is industrially useful. Specifically, the resin composition of the present embodiment can be used for applications including a photosensitive film, a photosensitive film with a support, a prepreg, a resin sheet, a circuit substrate (applications for a laminate, applications for a multilayer printed wiring board, and the like), a solder resist, an underfill material, a die bonding material, a semiconductor sealing material, a hole filling resin, and a component embedding resin.

The invention claimed is:

1. A compound (A) represented by the following formula (1):

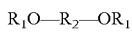   (1)

wherein each $R_1$ independently represents a group represented by the following formula (2), or a hydrogen atom, and $R_2$ represents a linear or branched alkylene group having 1 to 16 carbon atoms, or a linear or branched alkenylene group having 2 to 16 carbon atoms; provided that at least one $R_1$ is a group represented by the following formula (2):

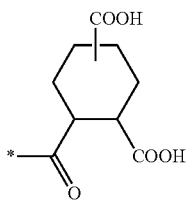   (2)

wherein -* represents a bonding hand.

2. The compound (A) according to claim 1, wherein at least one $R_1$ is a group represented by the following formula (3):

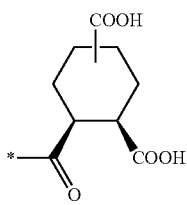   (3)

wherein -* represents a bonding hand.

3. A method for producing the compound (A) according to claim 1, comprising of reacting an alcohol compound represented by the following formula (4) with an acid anhydride represented by the following formula (5):

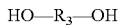   (4)

wherein $R_3$ represents a linear or branched alkylene group having 1 to 16 carbon atoms, or a linear or branched alkenylene group having 2 to 16 carbon atoms

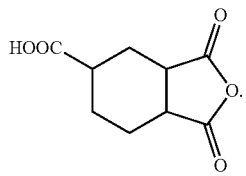   (5)

4. The production method according to claim 3, wherein the acid anhydride represented by the above formula (5) comprises an acid anhydride represented by the following formula (6):

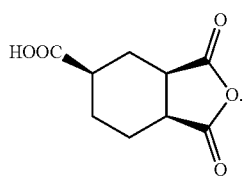   (6)

5. A resin composition comprising the compound (A) according to claim 1.

6. The resin composition according to claim 5, further comprising a bismaleimide compound (B) comprising a constituent unit represented by the following formula (7), and maleimide groups at both ends of the molecular chain:

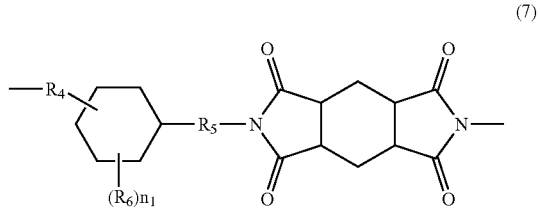   (7)

wherein $R_4$ represents a linear or branched alkylene group having 1 to 16 carbon atoms, or a linear or branched alkenylene group having 2 to 16 carbon atoms; $R_5$ represents a linear or branched alkylene group having 1 to 16 carbon atoms, or a linear or branched alkenylene group having 2 to 16 carbon atoms; each $R_6$ independently represents a hydrogen atom, a linear or branched alkyl group having 1 to 16 carbon atoms, or a linear or branched alkenyl group having 2 to 16 carbon atoms; and each $n_1$ independently represents an integer of 1 to 10.

7. The resin composition according to claim 5, further comprising at least one maleimide compound (C) selected from the group consisting of a compound represented by the following formula (8), a compound represented by the following formula (9), a compound represented by the following formula (10), a compound represented by the following formula (11), a compound represented by the following formula (12), and a compound represented by the following formula (13):

(8)
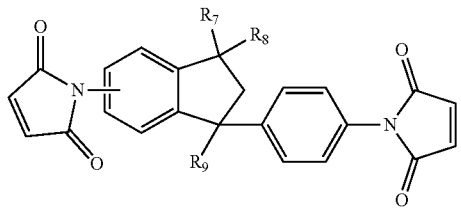

wherein $R_7$, $R_8$ and $R_9$ each independently represent a hydrogen atom, or a linear or branched alkyl group having 1 to 8 carbon atoms and optionally having a substituent;

(9)
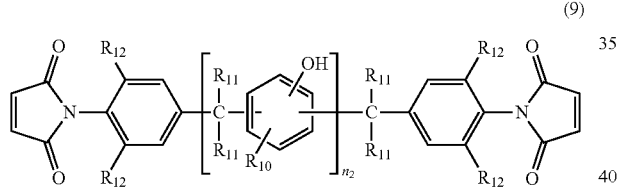

wherein $R_{10}$, $R_{11}$ and $R_{12}$ each independently represent a hydrogen atom, a hydroxyl group, or a linear or branched alkyl group having 1 to 6 carbon atoms and optionally having a substituent; and $n_2$ represents an integer of 1 to 10;

(10)
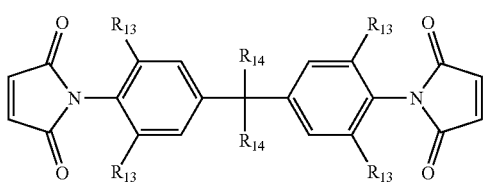

wherein each $R_{13}$ independently represents a hydrogen atom, a methyl group, or an ethyl group; and each $R_{14}$ independently represents a hydrogen atom or a methyl group;

(11)
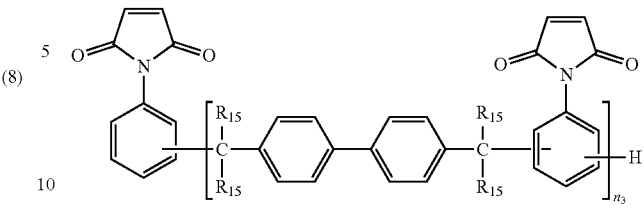

wherein each $R_{15}$ independently represents a hydrogen atom or a methyl group; and $n_3$ represents an integer of 1 to 10;

(12)
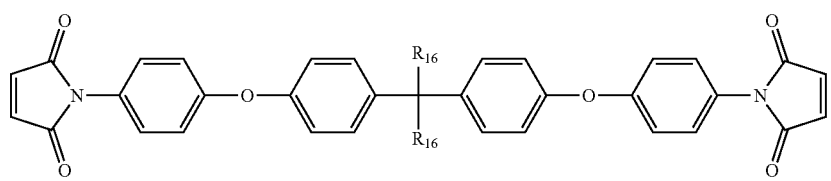

wherein each $R_{16}$ independently represents a hydrogen atom, a methyl group, or an ethyl group;

(13)
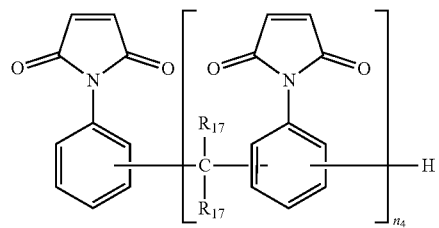

wherein each $R_{17}$ independently represents a hydrogen atom or a methyl group; and $n_4$ represents an integer of 1 to 10.

8. The resin composition according to claim 5, further comprising a photo initiator (D).

9. The resin composition according to claim 8, wherein the photo initiator (D) comprises a compound represented by the following formula (14):

(14)
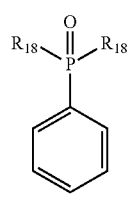

wherein each $R_{18}$ independently represents a group represented by the following formula (15) or a phenyl group;

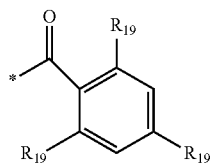

(15)

wherein -* represents a bonding hand, and each $R_{19}$ independently represents a hydrogen atom or a methyl group.

10. A resin sheet comprising:

a support; and a resin layer disposed on one surface or both surfaces of the support, wherein the resin layer comprises the resin composition according to claim 5.

11. The resin sheet according to claim 10, wherein the resin layer has a thickness of 1 to 50 μm.

12. A multilayer printed wiring board comprising:

an insulation layer; and a conductor layer formed on one surface or both surfaces of the insulation layer, wherein the conductor layer comprises the resin composition according to claim 5.

13. A semiconductor device comprising the resin composition according to claim 5.

* * * * *